United States Patent [19]

Neill et al.

[11] Patent Number: 5,583,210
[45] Date of Patent: Dec. 10, 1996

[54] METHODS AND COMPOSITIONS FOR CONTROLLING PLANT DEVELOPMENT

[75] Inventors: John Neill, Des Moines; Dorothy A. Pierce, Urbandale; Andrew M. Cigan, Des Moines, all of Iowa

[73] Assignee: Pioneer Hi-Bred International, Inc., Des Moines, Iowa

[21] Appl. No.: 33,797

[22] Filed: Mar. 18, 1993

[51] Int. Cl.$^6$ .......................... C12N 15/29; C12N 15/02; A01H 5/00
[52] U.S. Cl. .................... 536/23.6; 536/23.5; 435/172.3; 435/240.4; 435/320.1; 800/205
[58] Field of Search ................................. 536/23.6, 23.5; 435/172.3, 240.4, 320.1; 800/205

[56] References Cited

U.S. PATENT DOCUMENTS 5,107,065  4/1992  Shewmaker et al. .................... 800/205

OTHER PUBLICATIONS

EMBL Sequence Database Rel. 33 Acc. No. Z15157 (Oct. 12, 1992) A. thaliana mRNA for Wilms' tumor suppressor homolog.
EMBL Sequence Database Rel. 31 Acc. No. X64621 (Feb. 28, 1992) O. sativa R22 mRNA.
Rivera–Madrid, et al., Nucleotide sequence of an *Arabidopsis thaLiana* cDNA clone encoding a homolog to a suppressor of wilms' tumor, *Plant Physiology*, May, 1993, 102
Kamada, I., et al., Transgenic tobacco plants expressing rgp1, a gene encoding a ras–related GTP–binding proteing from rice, show distinct morphological characteristics, *Plant Journal*, 2:799–807, 1992.
Hilson, P., et al., Yeast RAS2 affects cell viability, mitotic division and transient gene expression in Nicotiana species, *Plant Molecular Biology*, 14:669–685, 1990.
Koltunow, A. M., et al., "Different Temporal and Spatial Gene Expression Patterns Occur During Anther Development", The Plant Cell, 2:1201–1224 (1990).
Jacobs, T., et al., "Control of the Cell Cycle", Developmental Biology, 153:1–15 (1992).
Van Den Ouweland, A., et al., "Identification and Characterization of a New Gene in the Human Xq28 Region", Human Molecular Genetics, 1(4):269–273 (1992).
Dowdy, S., et al. "The Isolation and Characterization of a Nevel cDNA Demonstrating and Altered mRNA Level in Nontumorigenic Wilms' Microcell Hybrid Cells", Nucleic Acids Research, 19(20):5763–5769 (1992).
Garnaat et al., "Isolation and Transient Assay of Tobacco Anther Specific Promoters", The International Society for Plant Molecular Biology, 393 (1991).
Ron et al., "pGSTag–A Versatile Expression Plasmid for Enzymatic Labeling of Recombinant Proteins", Bio Tech, 13:866–869 (1992).
Gardner et al., "The Complete Nucleotide Sequence of an Infectious Clone of Cauliflower Mosaic Virus by M1 3mp7 Shotgun Sequencing", Nucleic Acids Res., 9:2871–2888 (1981).
Walden et al., "Techniques in Plant Molecular Biology—Progress and Problems", Eur. J. Biochem., 192:563–576 (1990).
An et al "Functional Analysis of the 3' Control Region of the Potato Wound–Inducible Proteinase Inhibitor II Gene", Plant Cell, 1:115–122 (1989).
Colasanti, J. et al., "Isolation and Characterization of cDNA Clones Encoding a Functional $p34^{cdc2}$ Homologue From Zea Mays", Proc. Natl. Acad. Sci. USA, 88:3377–3381 (1991).
Ow et al., "Transient and Stable Expression of the Firefly Luciferase Gene in Plant Cells and Transgenic Plants", Science, 234:856–859 (1986).
Gallie et al., "The 5'–Leader Sequence of Tobacco Mosaic Virus RNA Enhances the Expression of Foreign Gene Transcripts in vitro and in vivo", Nucleic Acids Res., 8:3257–3273 (1987).
Yanisch–Perron et al., "Improved M13 Phage Cloning Vectors and Host Strains: Nucleotide Sequences of the M13mp 18 and pUC19 Vectors", Gene, 33:103–119 (1985).
Smith et al., "Single–Step Purification of Polypeptides Expressed in Escherichia coli as Fusions with Glutathione S–Transferase", Gene, 67:31–40 (1988).
Rivera et al (12 Oct. 1992) GenBank Locus ATWILMTSH, Accession Z 15157.
Berthomieu et al (17 Nov. 1992) GenBank Locus ATTS 0848, Accession Z18472.
Kim (28 Feb. 1992) GenBank Locus OSR 22 CDNA, Accession X46621.
Bird et al (24 Jul. 1992) EMBL ID/Accession No. Q22956.
Barker et al (17 Oct. 1991) EMBL ID/Accession No. N50182.
Majeau et al (19 May 1992) GenBank Locus TOBCLCAA, Accession M94135.
Hershey et al (23 Jan. 1991) EMBL ID/Accession No. Q05988.

Primary Examiner—Patricia R. Moody
Attorney, Agent, or Firm—Foley & Lardner

[57] ABSTRACT

A family of genes has been found in plants, said genes encoding a family of developmental proteins that have homologous structures to the mammalian QM genes. Recombinant molecules which include the QM genes in plants are useful to transform cells and regenerate plants that, as a result, have altered developmental pathways. Methods of producing male sterile plants use recombinant molecules containing either the QM sense genes or antesense genes with appropriate promoters.

11 Claims, 12 Drawing Sheets

FIG. 1

```
  1 GGATCCGCCGACACCGACTGCCTACCTCAGCTGCCGTCGCCATGGGCAGAAGGCCTGCTA
    CCTAGGCGGCTGTGGCTGACGGATGGAGTCGACGGCAGCGGTACCCGTCTTCCGGACGAT
                                            M  G  R  R  P  A  R -

61 GATGCTATCGCCAGATCAAGAACAAGCCGTGCCCTAAGTCCAGGTACTGCCGTGGTGTCC
    CTACGATAGCGGTCTAGTTCTTGTTCGGCACGGGATTCAGGTCCATGACGGCACCACAGG
     C  Y  R  Q  I  K  N  K  P  C  P  K  S  R  Y  C  R  G  V  P -

121 CTGACCCCAAGATCAGGATCTACGATGTCGGGATGAAGAGGAAGGGTGTTGATGAGTTCC
    GACTGGGGTTCTAGTCCTAGATGCTACAGCCCTACTTCTCCTTCCCACAACTACTCAAGG
     D  P  K  I  R  I  Y  D  V  G  M  K  R  K  G  V  D  E  F  P -

181 CCTACTGTGTGCACCTTGTCTCTTGGGAGAGGGAGAATGTCTCCAGTGAGGCGCTCGAGG
    GGATGACACACGTGGAACAGAGAACCCTCTCCCTCTTACAGAGGTCACTCCGCGAGCTCC
     Y  C  V  H  L  V  S  W  E  R  E  N  V  S  S  E  A  L  E  A -

241 CTGCCCGCATTGTCTGTAACAAGTACATGACCAAGTCTGCAGGAAAGGATGCCTTCCACC
    GACGGGCGTAACAGACATTGTTCATGTACTGGTTCAGACGTCCTTTCCTACGGAAGGTGG
      A  R  I  V  C  N  K  Y  M  T  K  S  A  G  K  D  A  F  H  L -

301 TTAGGGTCCGGGTTCACCCGTTCCATGTCCTCCGTATCAACAAGATGCTTTCCTGTGCCG
    AATCCCAGGCCCAAGTGGGCAAGGTACAGGAGGCATAGTTGTTCTACGAAAGGACACGGC
     R  V  R  V  H  P  F  H  V  L  R  I  N  K  M  L  S  C  A  G -

361 GGGCTGATAGGCTCCAGACTGGAATGAGGGGTGCCTTTGGCAAGCCTCAGGGCACCTGTG
    CCCGACTATCCGAGGTCTGACCTTACTCCCCACGGAAACCGTTCGGAGTCCCGTGGACAC
     A  D  R  L  Q  T  G  M  R  G  A  F  G  K  P  Q  G  T  C  A -

421 CTAGGGTGGACATTGGTCAGGTCCTCCTTTCCGTGCGGTGCAAGGAACAACAATGCTGCC
    GATCCCACCTGTAACCAGTCCAGGAGGAAAGGCACGCCACGTTCCTTGTTGTTACGACGG
     R  V  D  I  G  Q  V  L  L  S  V  R  C  K  E  Q  Q  C  C  P -

481 CATGCCAGCGAAGTCTGCGTCGCGCTAAGTTCAAGTTCCCTGCCCGCCAGAAGATCATTG
    GTACGGTCGCTTCAGACGCAGCGCGATTCAAGTTCAAGGGACGGGCGGTCTTCTAGTAAC
     C  Q  R  S  L  R  R  A  K  F  K  F  P  A  R  Q  K  I  I  E -

541 AGAGCAGAAAGTGGGGCTTCACCAAGTTCAGCCGCGCTGACTACCTGAAGTACAAGAGCG
    TCTCGTCTTTCACCCCGAAGTGGTTCAAGTCGGCGCGACTGATGGACTTCATGTTCTCGC
     S  R  K  W  G  F  T  K  F  S  R  A  D  Y  L  K  Y  K  S  E -

601 AGGGCAGAATTGTTCCTGATGGTGTCAACGCAAAGCTGCTCGCCAACCACGGCAGACTTG
    TCCCGTCTTAACAAGGACTACCACAGTTGCGTTTCGACGAGCGGTTGGTGCCGTCTGAAC
     G  R  I  V  P  D  G  V  N  A  K  L  L  A  N  H  G  R  L  E -

661 AGAAGCGTGCTCCTGGGAAGGCTTTCCTCGATGCCGTTGCTTAAGTGCGGATGCGAATCC
    TCTTCGCACGAGGACCCTTCCGAAAGGAGCTACGGCAACGAATTCACGCCTACGCTTAGG
     K  R  A  P  G  K  A  F  L  D  A  V  *

721 TGACGTTTTGCTTTAGCGTATCTTACTTTGCTTCGTGGAACATGAATTTCAAGTGTTTTG
    ACTGCAAAACGAAATCGCATAGAATGAAACGAAGCACCTTGTACTTAAAGTTCACAAAAC

781 AGGGTATTACAGTGCCTTATGTGAACTTGCCTATCTTGTGCTGAACATCGGAATGTATCC
    TCCCATAATGTCACGGAATACACTTGAACGGATAGAACACGACTTGTAGCCTTACATAGG

841 TCCGAGTATGTTTAATCGCATTAATTTTATTGGGAAATTGGTTGCGGAACAATGTCCAAT
    AGGCTCATACAAATTAGCGTAATTAAAATAACCCTTTAACCAACGCCTTGTTACAGGTTA

901 TTAACTCGAATTTGATTTCAACACGGTCTTTTCTTT
    AATTGAGCTTAAACTAAAGTTGTGCCAGAAAAGAAA
```

FIG. 2

```
  1 MGRRPARCYRQIKNKPCPKSRYCRGVPDPKIRIYDVGMKRKGVDEFPYCV 50
  1 MGRRPARCYRYCKNKPYPKSRFCRGVPDAKIRIFDLGRKKAKVDEFPLCG 50

51 HLVSWERENVSSEALEAARIVCNKYMTKSAGKDAFHLRVRVHPFHVLRIN 100
 51 HMVSDEYEQLSSEALEAARICANKYMVKSCGKDGFHIRVRLHPFHVIRIN 100

101 KMLSCAGADRLQTGMRGAFGKPQGTCARVDIGQVLLSVRCKEQQCCPCQR 150
101 KMLSCAGADRLQTGMRGAFGKPQGTVARVHIGQVIMSIRTKLQNKEHVIE 150

151 SLRRAKFKFPARQKIIESRKWGFTKFSRADYLKYKSEGRIVPDGVNAKLL 200
151 ALRRAKFKFPGRQKIHISKKWGFTKFNADEFEDMVAEKRLIPDGCGVKYI 200

201 ANHGRLEKRAPGKAFLDAVA 220
201 PSRGPLDKWRALHS...... 214
```

METHODS AND COMPOSITIONS FOR CONTROLLING PLANT DEVELOPMENT

BACKGROUND OF THE INVENTION

The structure and genetic coding sequences of a family of developmental proteins in plants have homology to mammalian QM proteins and to genes encoding the proteins. Recombinant molecules comprising plant QM coding regions and suitable promoters, are used to produce a transformed plant with altered development. The altered development causes male sterility.

The expression of most, if not all, plant genes can be considered to be related in some way to plant development. Many classes of genes are known to respond to development signals involved in cell differentiation, formation of tissues and organs, or in controlling plant growth. There are several well-characterized examples: genes that are regulated by light (such as rbcS and cab gene families), or by hormones and genes that express specifically in anthers, roots, seeds or leaves, or in specific cell types in these tissues (See Edwards and Coruzzi, 1990 and Kuhlmeier, Green and Chua, 1987 for reviews). Other types of genes are known to regulate the expression of yet other genes, such as the maize regulatory gene Opaque2 that codes for a transcriptional activator which regulates the expression of 22kd zein genes (Schmidt et al., 1992, Ueda et al., 1992) or the C1 and R genes in maize that code for transcriptional activators that regulate the expression of A1 and BZ1 (Klein et al., 1989).

A very new area of research in plants includes the identification and isolation of genes from plants, which, based on their homology to genes from animal and yeast systems, are believed to be involved in the control of basic cell processes such as cell division (See Jacobs, 1992 for a review). An example of such a gene is the homologue of the yeast cdc2 gene which has been cloned from maize (Colasanti, et al., 1991). In the future, there are certain to be additional genes identified in plants which control other basic cellular or developmental processes.

In mammals, developmental proteins have been implicated in abnormal cell division such as characterizes the malignant state. For example, Wilms' tumor is a pediatric tumor of the kidney which arises in embryonic blastoma cells and occurs in both sporadic and hereditary forms. Three groups have reported the cloning of two distinct genes which are associated with Wilms' tumor. The first, WT1, encodes a zinc finger protein belonging to the early growth response (EGR) gene family and maps to the llp13 locus in humans, which is often deleted in tumorigenic cells (Call et al., 1990, Gessler et al., 1990). The second gene, termed QM, was originally cloned by Dowdy et al., *Nuc. Acids Res.,* 19: 5763–5769, (1991) through the use of subtractive hybridization using cDNAs and RNA derived from tumorigenic and non-tumorigenic Wilms' microcell hybrid cells, respectively. This gene was shown to be expressed at the RNA level in virtually all normal tissues examined in the mouse but was lacking in Wilms' tumorigenic cell lines.

The protein encoded by this gene is 25 kD in size and is very basic with a pI of approximately 12.0. Dowdy also demonstrated that QM is a member of a family of genes in a number of mammals, particular primates. van den Ouweland et al. (1992) cloned the QM gene from a human Xqter chromosome library and showed that this gene was 100% similar to the previously cloned QM gene. The expression of the QM gene has been demonstrated in the mouse (Dowdy et al., 1991), has been cloned in the chicken, and with data from van den Ouweland et al., suggests that this gene is conserved across a large phylogenetic range. It was postulated that QM may be involved in maintenance of the non-tumorigenic phenotype (Dowdy et al. 1991). It would not be expected to find the QM gene in plants, which do not have comparable phenotypes.

Discovery of genes which would alter plant development would be particularly useful in developing genetic methods to induce male sterility because other methods currently available have serious shortcomings (e.g., detasseling, CMS, SI, and the like).

Production of hybrid seed for commercial sale is a large industry. Hybrid plants grown from hybrid seed benefit from the heterotic effects of crossing two genetically distinct breeding lines. The agronomic performance of this offspring is superior to both parents, typically in vigor, yield and uniformity. The better performance of hybrid seed varieties compared to open-pollinated varieties makes the hybrid seed more attractive for farmers to plant and thereby commands a premium price in the market.

In order to produce hybrid seed uncontaminated with self-seed, pollination control methods must be implemented to ensure cross-pollination and not self-pollination. Pollination control mechanisms can be mechanical, chemical or genetic.

A mechanical method for hybrid seed production can be used if the plant species in questions has spatially separate male and female flowers or separate male and female plants. The corn plant, for example, has pollen producing male flowers in an inflorescence at the apex of the plant and female flowers in the axils of leaves along the stem. Outcrossing is assured by mechanically detasselling the female parent to prevent selfing. Even though detaseling is currently used in hybrid seed production, the process is labor intensive and costly (yield loss is incurred).

Most major crop plants of interest, however, have both functional male and female organs within the same flower so emasculation is not a simple procedure. It is possible to remove by hand the pollen forming organs before pollen shed, however, this form of hybrid seed production is extremely labor intensive and, hence, expensive. Seed is produced in this manner if the value and amount of seed recovered warrants the effort.

A second general method of producing hybrid seed is to use chemicals that kill or block viable pollen formation. These chemicals, termed gametocides, are used to impart a transitory male-sterility. Commercial production of hybrid seed by use of gametocides is limited by the expense and availability of the chemicals and the reliability and length of action of the applications. These chemicals are not effective for crops with the extended flowering period because new flowers will be produced that will not be affected. Repeated application of chemicals is impractical because of costs.

Many current commercial hybrid seed production systems for field crops rely on a genetic method of pollination control. Plants that are used as females either fail to make pollen, fail to shed pollen or produce pollen that is biochemically unable to effect self-fertilization. Plants that are unable (by several different means) to self pollinate biochemically are termed self-incompatible. Difficulties associated with the use of self-incompatibilities include availability and propagation of the self-incompatible female line and stability of the self-compatibility. In some instances, self-incompatibility can be overcome chemically or immature buds can be pollinated by hand before the biochemical mechanism that blocks pollen is activated. Self-incompatible systems that can be deactivated are often very vulnerable to stressful climatic conditions that break or reduce the effectiveness of the biochemical block to self-pollination.

Of more widespread interest for commercial seed production are systems of pollen control based genetic mechanisms causing male sterility. These systems are of two general types: (a) genic male sterility, which is the failure of pollen formation because of one or more nuclear genes or (b) cytoplasmic-genetic male sterility (commonly called cytoplasmic male sterility or CMS) in which pollen formation is blocked or aborted because of a defect in a cytoplasmic organelle (mitochondrion).

Nuclear (genic) sterility can be either dominant or recessive. A dominant sterility can only be used for hybrid seed information if propagation of the female line is possible (for example, via in vitro clonal propagation). A recessive sterility could be used if sterile and fertile plants are easily discriminated. Commercial utility of genic sterility systems is limited however by the expense of clonal propagation and roguing the female rows of self-fertile plants.

Many successful hybridization schemes involve the use of CMS. In these systems, a specific mutation in the cytoplasmically located mitochondrion can when in the proper nuclear background, lead to the failure of mature pollen formation. In some instances, the nuclear background can compensate for the cytoplasmic mutation and normal pollen formation occurs. The nuclear trait that allows pollen formation in plants with CMS mitochondria is called restoration and is the property of specific "restorer genes". Generally, the use of CMS for commercial seed production involves the use of three breeding lines, the male-sterile line (female parent), a maintainer line which is isogenic to the male-sterile line but contains fully functional mitochondria and the male parent line.

The male parent line may carry the specific restorer genes (usually designated a restorer line) which then imparts fertility to the hybrid seed. For crops, such as vegetable crops for which seed recovery from the hybrid is unimportant, a CMS system could be used without restoration. For crops for which the fruit or seed of the hybrid is the commercial product then the fertility of the hybrid seed must be restored by specific restorer genes in the male parent or the male-sterile hybrid must be pollinated. Pollination of non-restored hybrids can be achieved by including with hybrids a small percentage of male fertile plants to effect pollination. In most species, the CMS trait is inherited maternally (because all cytoplasmic organelles are inherited from the egg cell only), which can restrict the use of the system. Although still used for a number of crops, limitations of CMS systems have a tendency to break down with prolonged use. Generally, male sterility is less than 100% effective. One particular CMS type in corn (T-cytoplasm) confers sensitivity to infection by a particular fungus.

A search for methods of altering development in plants, for example, to produce male sterile plants, revealed an exceptionally suitable family of developmental proteins.

SUMMARY OF THE INVENTION

The present invention relates methods and compositions for altering plant development. The methods use genetic constructs including the QM gene in plants.

The QM gene has been described in mammals in relation to tumors, being present empressed in normal cells, but not empressed in tumor cells. The gene is likely to be down-regulated in tumors, for example in Wilms' tumor in humans. A gene related to mammalian oncogenesis would not be expected to have a homologue in plants, because comparable developmental abnormalities do not occur. Tumors are known to occur in certain plant species but these are specifically caused by infection by exogenous agents such as Agrobacterium or other pathogens. Yet, a polynucleotide was isolated from the maize genome that unexpectedly showed homology with the nucleotide sequence of the mammalian QM gene. That polynucleotide from maize is referred to hereon as "$QM_m$."

The protein encoded by the maize polynucleotide is a developmental protein. Developmental proteins include proteins that are expressed during development in response to a regulatory signal such as a hormone, and proteins that regulate developmental pathways. The QM gene in plants therefore is useful in the context of controlling development, for example, development of pollen. Interference with pollen development produces a male sterile plant. Developmental proteins are recognized by their ability to alter the result of normal development structure or function.

A cDNA prepared from a $QM_m$ polynucleotide consists essentially of 800–950 nucleotides, including an open reading frame (ORF) and flanking regions. The comparable mammalian cDNA generally is less than 800 nucleotides. The single open reading frame in the maize cDNA encodes a polypeptide of approximately 220 amino acids. In other species, an open reading frame in the QM cDNA isolated from humans, encodes a family of QM protein of approximately 214 amino acids. In general, a QM family of genes in plants ($QM_P$) encodes a protein characterized by a primary sequence of approximately 200–250 amino acids, and having the following properties.

More specifically, genes of the QM family each encodes a family of proteins that is characterized by the presence of three conserved regions in the amino acid sequence of the protein members of the family. In a maize QM protein, the first conserved region includes the first 20 amino acids positioned from the amino terminus; the second conserved region includes the amino acid sequence from residues 50 to 60, and forms an amphipathic helix region in the QM protein; the third conserved region is located at residues 98–135. These three conserved regions exhibit a high degree of homology to corresponding regions that are characteristic of their mammalian counterparts. "High degree of homology" is defined here to denote that at least 80% of the amino acids at corresponding positions, as defined in reference to the amino terminus of the sequence are identical.

The overall homology of a plant QM amino acid sequence, relative to a mammalian counterpart, is generally at least 50%. (The differences between plants and mammals occur in the region from approximately residue 135 (relative to the N-terminal) to the C-terminal end of the protein.

The nucleotide sequence positions from the that encode the conserved region in the maize QM gene are located at approximately positions 30–100, positions 210–250 and positions 330–400 from the N-terminus. Hybridization probes prepared from these regions will hybridize to the comparable mammalian QM sequences under stringent conditions. Oligonucleotide probes prepared from the conserved region are useful to detect new QM genes in plants under low stringency conditions, for example, using 50% formamide, 5X SSC (0.75 M NaCl), at 37° C. The coding regions of the maize sequence show approximately 64% homology to the human QM sequence overall.

Because of "wobble" in the third position of each codon in the nucleotide sequence, a functionally similar protein would be expected to be encoded with as much as 36% overall divergence between the nucleotide coding regions. In the same species, a sequence encoding at least the three conserved regions is expected to encode a functionally equivalent protein. This is not necessarily true of cross-species comparisons, where protein function is interrelated with biochemical pathways characteristic of the species. However, both the plant and the mammalian QM proteins have major effects on developmental processes.

At least two QM polynucleotides, and as many as six, are distinguishable by Northern blot analysis of maize preparations. An illustrative embodiment of a polynucleotide encoding a QM protein is shown in FIG. 1 (SEQ ID NOS: 1 and 2) for maize. Oligonucleotide primers developed from this sequence are used to amplify the DNA in the open reading frame. These primers are useful in detection of the tobacco homologue. The amino acid sequence corresponding to FIG. 1 (SEQ ID NO: 2) is shown in FIG. 2.

An isolated and purified plant QM protein has an estimated molecular weight of approximately 25 kD and a PI of approximately 11.0. A protein deduced from the cDNA sequence will be free of other proteins when prepared synthetically or by recombinant methods. Isolated and purified QM proteins and epitopic fragments thereof are useful in preparing antibodies. These antibodies in turn are useful for diagnosis of developmental problems and the analysis of developmental pathways in plants. The location and level of expression of the QM protein is useful in determining how to alter development. For example, the antibodies developed to QM are useful to determine if and when the protein is turned on in specific cells or tissues of the plant. This information is useful in developing methods for interfering with or enhancing developmental pathways, including those related to pollen development. Such information is useful in developing superior plants, or male sterile plants, for example.

Isolated and purified QM proteins in plants are also useful in analyzing protein-protein interactions. For these purposes, labeled protein probes are developed. A fusion protein including the QM protein is prepared in *E. coli*, for example, isolated, labelled and used in detecting protein interactions during development. See Smith & Johnson (1988), Gene 67:31–40; Ron & Dressler (1992) BioTech 13: 866–69.

A recombinant DNA molecule is prepared comprising the QM gene in the sense orientation (the orientation such that the normal mRNA is transcribed and is used as a template to translate the normal QM gene protein, and a promoter capable of regulating transcription of said DNA in a plant cell. The recombinant DNA molecule can alternatively encode the QM gene in the antisense orientation. This molecule contains the QM gene cloned in the opposite direction such that the minus or non-coding strand is transcribed. No QM gene product is translated, but a MRNA transcript complementary to the QM mRNA is produced which is inhibitory to the translation of the plants own QM mRNA, thus decreasing the amount of QM protein produced. (See U.S. Pat. No. 5,107,065, the contents of which are incorporated by reference).

The promoter in the construct may be a cell-or tissue-specific promoter, so that the gene may be expressed in specific cells or tissues. For example, in a method to produce a male sterile plant, an anther specific or tapetal-specific promoter is preferred. Anther tissue and tapetal cells are examples of a tissue or cell that is crucial to development of pollen. Anther tissue includes support cells and developing microspores, and excludes mature pollen. A QM gene construct can be effective in altering development whether expressed in a sense or an antisense orientation. If there are genes and processes in anther tissue which are or can be regulated by QM, a sense QM construct could affect development by altering the timing of regulation by QM or affect development by overexpression of the QM protein. Correspondingly, if QM or any genes which can be regulated by QM are essential for normal anther development, expression of an antisense QM construct could affect development by interfering with normal QM expression.

The promoter in the construct may be an inducible promoter, so that expression of the sense or antisense molecule in the construct can be controlled by exposure to the inducer. Exemplary of such an inducer is a plant hormone.

Altering development is particularly useful for producing a male sterile plant. A method of producing a male sterile plant is to transform a plant cell with a recombinant molecule comprising the sense gene for the QM plant protein, or an antisense molecule directed to the QM gene. An appropriate promoter is selected depending on the strategy for developmental control. For example, a strategy is to overexpress the QM gene selectively in anther tissue by using an anther specific promoter. To produce a male sterile plant, the transformed cell would be regenerated into a plant, pursuant to conventional methodology.

A transgenic plant containing the QM gene construct can be regenerated from a culture transformed with the same construct. The culture includes an aggregate of cells, a calli, or derivatives thereof that are suitable for culture.

A plant is regenerated from a transformed cell or culture by methods disclosed herein that are known to those of skill in the art. Seed is obtained from the regenerated plant or from a cross between the regenerated plant and a suitable plant of the same species using breeding methods known to those of skill in the art.

FIG. 1 illustrates the nucleotide and derived amino acid sequence of clone 10–15 (SEQ ID NOS. 1 and 2). The cDNA clone was 936 nucleotides in length and contained a single open reading frame encoding a polypeptide of 25,138 daltons. This polypeptide is very basic, having a calculated pI of 11.0, with the basic residues being distributed throughout the protein. In the search for homology with other previously characterized genes, the amino acid sequence encoded by clone 10–15 was used to survey the GenBank database using the TFASTA program of Genetic Computer Group (GCG, Devereux et al., 1984). This analysis yielded a score of 716 with the human gene QM. When the amino acid sequence encoded by clone 10–15 (SEQ ID NO: 2) was aligned with the amino acid sequence of the human gene (SEQ ID NO: 3) (FIG. 2), several regions of interest are seen. First, is the high degree of conservation of the amino-terminal region, where the first ten amino acid residues are conserved. The second region, again conserved in the two proteins, is between residues 50 and 61 which forms a putative amphipathic helix.

The presence of a 59 residue stretch of highly conserved amino acid argues strongly for a conserved function within this region. The carboxy-terminal region is poorly conserved and may not be as important in the function of the protein. Northern blot analysis of RNA isolated from leaf and root tissues from seven day corn seedlings demonstrates that cDNA from clone 10–15 is expressed in both with roots and leaves showing roughly the same level of expression. In additional northern blots, this gene was found to be expressed in anthers and earshoots.

Southern blot analysis demonstrates that the maize homolog is a member of a small family of approximately 4 to 6 members in maize.

METHOD OF CAUSING MALE STERILITY IN PLANTS

USE OF QM GENE IN SENSE ORIENTATION: The nucleotide segment of the QM gene is fused at its upstream (5') end to a promoter which is known to be specific for, or show a strong preference for expression in, a tissue or cell that is critical for pollen development. The anther is an example of such a tissue. A tapetal cell or developing microspore is an example of a suitable cell. The segment is fused at its downstream (3') end to suitable transcription terminator and polyadenylation signals also known to function in that cell. Preferred promoters would be SGB6 for maize and TA39 (from tobacco) and the promoter Bp (from *B. napus* for dicots.

The present invention relates to a method for producing male sterile plants and hybrid seed, to genetic material used to impart the male sterility trait and to new products produced by said method, namely, genetically transformed plants carrying the male sterile trait, male sterile plants and hybrid seed produced by pollinating said plants with pollen from male fertile plants.

BRIEF DESCRIPTION OF THE DRAWINGS

FIG. 1. Nucleotide sequence and the encoded amino acid sequence of the cDNA clone 10–15 (SEQ ID NOS: 1 and 2) which encodes the maize QM homolog.

FIG. 2. Amino acid alignment analysis of the maize QM homolog (upper sequence, SEQ ID NO: 2) with the human QM amino acid sequence (SEQ ID NO: 3).

DESCRIPTION OF THE PREFERRED EMBODIMENTS

Figure 3:
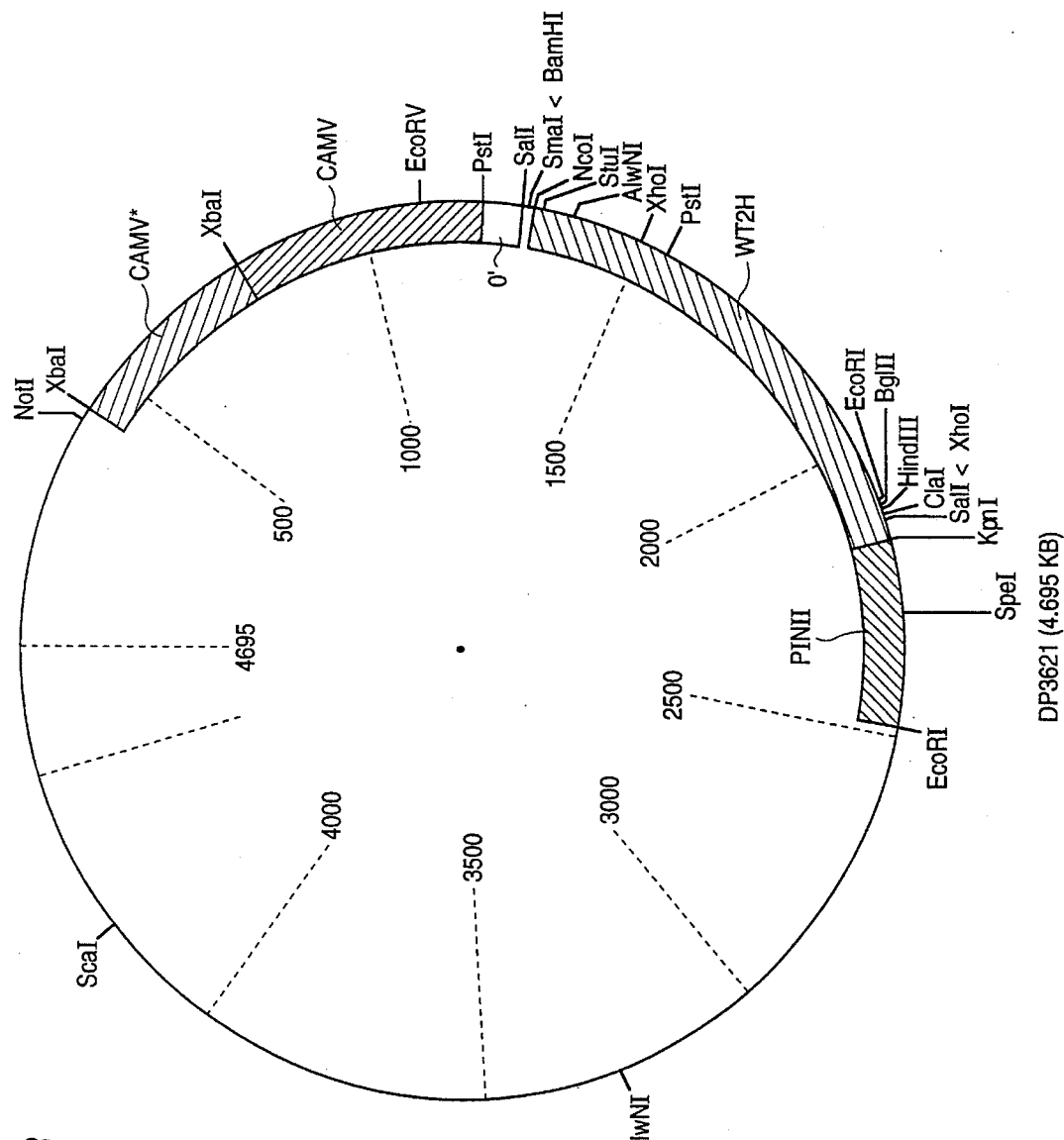
FIG. 3. Restriction map of Dp3621.

A human, constitutively expressed gene, which is thought to play a role in maintenance of the non-tumorigenic state, has been shown to be absent in Wilms' tumorigenic cells lines. This gene, which is present as a gene family in humans and rodents, has been demonstrated in a number of diverse mammalian species. A gene has been cloned from maize which encodes a protein having a high degree of homology with the human QM protein (approximately 67%). The maize gene encodes a polypeptide of 25 kD of which basic residues comprise 22% of the protein. This gene is expressed in all maize tissues examined by northern blot analysis and is a member of a plant gene family.

Example 1: Interference with Normal Development of Tobacco Plants by Transformation with the QMp Gene QMp refers to the QM gene derived from a plant. $Qm_m$ refers to the QM gene derived from maize. Tobacco cells (cv. xanthi) were germinated under sterile conditions. After approximately 7 to 10 days under light at 28° C., the cotyledons and first leaves were removed aseptically and cut into fourths (approximately 1–2 mm square sections) and placed onto sterile filter paper discs saturated with medium containing 0.25 M sorbitol. The discs were incubated in the dark at 28° C. overnight. The next morning the tissue sections were bombarded by means of a biolistical apparatus to transform cells with an equal mixture of the $QM_m$ construct (sense construct or antisense construct) and plasmid containing the selectable marker (BAR gene). 0.1 μg of total DNA/5 bombardments. Following bombardment, the tissue was returned to the 28° C. incubation in the dark. After 48 hours the bombarded tissue was transferred to selection medium (BASTA) and placed under lights at 28° C. After about 2 weeks, small colonies began to appear, and continued to appear for about 1 week. The leaf pieces were transferred to regeneration medium which allowed leaves and plantlets to form. After the formation of plants, the young plantlets were transferred to rooting medium to allow root formation. After about 1–2 weeks, the plants were taken to the greenhouse for planting.

The sense construct did not yield as many colonies as did the control (selectable marker alone). In fact, many colonies formed but, subsequently died. Those that lived grew at a much slower rate than the controls. Most of the surviving calli generated from the colonies did not give rise to plants. Observations on the calli indicate they were having trouble forming or organizing a meristem to produce a plant. Most of those that did produce plants did so from growth of a distinct portion of the calli indicating a revertant sector (loss of the plasmid). The resulting plants were negative for the maize gene by PCR analysis. A plant was found to be positive for the plasmid, yet did produce a plant. However, this plant grew very slowly and did not produce roots by the time it was transferred to the greenhouse. It grew extremely slowly in the greenhouse for some time (approximately 1 month) after which it grew at a normal rate and appeared normal. The plant flowered and set seed in a fashion similar to normal plants, however, the seeds that were produced were abnormal looking, and in germination tests took greater than 2 weeks to germinate compared to 4–6 days for normal seed.

The calli derived from the antisense bombarded tissues showed completely different growth characteristics. The calli in several instances grew at a much accelerated rate and produced an abundance of vegetative growth. These calli produced plants at a near normal rate. The plantlets moved to regeneration and rooting medium produced roots at a rate faster than controls. The resulting plants appeared normal, flowered and set seed in a normal fashion. The seeds produced germinated normally and the plants appear normal.

The QM gene plays a role in development. In transformed tobacco, most likely, its presence prevents or inhibits meristem formation. When expressed QMs may "fix" a cell at a specific developmental stage. After the gene is turned on, the cell will no longer differentiate. Overexpression of the gene in tobacco calli inhibited the formation of meristem to generate plants. Overexpression may be lethal at higher concentrations.

The plant cells with constructs including the antisense molecules, were able to grow in some cases at accelerated rates. An interpretation of these results is that the antisense molecule was stopping the action of the tobacco QM gene product, and allowing differentiation to occur more readily and to produce the abundance of foliage seen on the calli. The experiment was repeated 3 times and basically the same observations were made in each experiment.

Example 2: Demonstration of microspore-specific gene expression by in situ hybridization This example illustrates a method for showing that an isolated DNA comprises a gene that exhibits microspore-specific expression. In particular, the results here demonstrate that expression of mRNAs related to a particular tobacco cDNA clone is localized to microspores of tobacco anthers.

An anther-specific tobacco cDNA clone, designated TA39, was obtained from Dr. Robert B. Goldberg of the Department of Biology, University of California, Los Angeles, Calif. This cDNA hybridizes to mRNA from tobacco anthers and not to mRNA from the pistil, petal, leaf or stem (Koltunow et al., 1990). The cDNA is 490 bases long, including a poly A+ tail of 42 bases (SEQ. ID. NO: 1 and FIG. 1). This cDNA hybridizes to two transcripts of 550 bases and 680 bases in Northern blots of RNA isolated from anthers. RNA dot blots have shown that TA39-related transcripts accumulate and decay with the same temporal sequence as five other anther-specific transcripts, all of which are localized within the tapetum (Koltunow et al., 1990).

Anthers of *Nicotinia tobacum* (cv Ky17) were collected at the tetrad stage and handled by standard cytological techniques (Berlyn and Miktha et al., 1976, BOTANICAL MICROTECHNIQUE AND CYTOCHEMISTRY, The Iowa State University Press, Ames, Iowa, Ch. 3, 4, and 5. Anthers were dehydrated in t-butanol and embedded in paraffin, then sliced into 8 μm thick sections and fixed to slides. DNA fragments of clone TA39 and another cDNA clone (LA2: an epidermis-specific mRNA) were excised from plasmids, purified by gel electrophoresis and labeled by nick translation with biotin-14-dATP, using the BioNick Labeling System (BRL) according to directions of the manufacturer. In situ hybridization of fixed anther sections with biotin labeled probes was carried out and detected using the DNA Detection System of BRL. In this system, streptavidin binds biotinylated probe DNA and biotinylated alkaline phosphatase, resulting in precipitation of nitroblue tetrazolium in cells in which the probe hybridizes to target nucleic acids.

Examination of these in situ hybridization analyses showed that the anther locules of the tested specimens contained tetrad stage microspores. In anther sections probed with TA39 DNA, only the tetrads accumulated tetrazolium dye. In contrast, anther sections probed with a control DNA (LA2) accumulated dye in the epidermal layer. This tissue-specific control demonstrates that the observed precipitation of dye in microspores of anther sections probed by TA39 DNA is not due to nonspecific retention of DNA or detection system components by the microspores.

Example 3: Isolation of genomic clones comprising sequences homologous to microspore-specific mRNA This example provides methods of isolation of genomic DNA clones comprising sequences homologous to any microspore-specific mRNA for which a nucleic acid probe is available. The approach described is useful for isolating microspore-specific regulatory sequences from any plant species which has microspore-specific mRNA that is homologous to such an available probe.

A genomic library of a selected plant, for instance a commercially available library of *N. tabacum*, var. NK326 DNA fragments (Clontech Laboratories, Inc., Palo Alto, Calif., catalog FL1070D), partially digested with MboI and cloned into the plasmid EMBL-3, was screened for clones having homology to cDNA clone TA39. Standard hybridization methods were used, such as are described in J. Sambrook et al., MOLECULAR CLONING (Cold Spring Harbor Laboratory Press, 1989). Candidate clones were purified by three or more cycles of picking plaques, replating, and reprobing with a TA39 cDNA insert, until consistently hybridizing plaques were either purified or shown not to be present.

Two distinguishable families of genomic tobacco DNA clones related to the TA39 cDNA clone were identified, each represented by two overlapping clones within each family. One clone of each family was selected for detailed characterization, designated clones 14B1 and 8B3. The region of homology with TA39 in each of these genomic clones, as well as the regions immediately upstream and downstream of these regions of homology, were mapped by restriction enzyme cleavage analysis and DNA hybridization.

These coding sequences and associated 5' presumptive regulatory regions were isolated as subclones and then further subcloned for sequencing. Thus, nested sets of deletions of each genomic clone were produced by using exoIII and mung bean nucleases supplied in a kit by Stratagene. The nested deletions were sequenced by the dideoxy chain termination method of Sanger with an automated DNA sequencer (Applied Biosystems 373A) at the Nucleic Acids Facility of the Iowa State University. The cDNA insert of TA39 was also sequenced for comparison. The TA39 cDNA sequence. Within the region of homology with the TA39 cDNA of a microspore-specific mRNA, genomic clone 8B3 is completely homologous with TA39, while the comparable portion of genomic clone 14B1 is about 90% homologous with TA39.

The starting points for transcription of the 14B1 and 8B3 genomic clones was mapped by primer extension experiments to a single nucleotide, 83 bases upstream of the putative translational start site. A perfect TATA box appears 31 bp upstream of the mapped start of transcription in each clone, and a major open reading frame of 110 amino acids is intact downstream of the start of transcription in both clones (i.e., at the position designated "+83" relative to the transcription initiation site). Both clones also have a polyadenylation recognition site, 29 bp and 37 bp downstream of a translational stop codon in clones 14B1 and 8B3, respectively.

Example 4: Testing for microspore-specific expression of a heterologous gene that is operatively linked to presumptive control sequences of genomic DNA clones This example illustrates the use of microspore-specific regulatory regions from genomic DNA clones to provide microspore-specific control of expression of a heterologous reporter gene in a transient gene expression assay.

The putative promoters of 8B3 and 14B1 were each fused to an open reading frame of a reporter gene (uidA) encoding beta-glucuronidase (GUS), followed by the 3' untranslated region of the proteinase II (pinII) gene from potato. In one version, comprising a "translational" fusion, each promoter was cloned from the beginning of the available upstream sequences to the start of translation at nucleotide +83. In another variation designated a "transcriptional" fusion, each promoter was cloned from the beginning of available upstream sequences to just beyond the start of transcription, at nucleotide +4. The latter constructs contained the non-translated leader of Tobacco Mosaic Virus (omega') between the promoter and uidA sequences. Translational gene fusions analogous to those containing the GUS reporter gene were also constructed for another model gene, the firefly luciferase coding region.

The uidA gene fusions were tested in transient expression assays on tobacco (cv. Petite Havana) stage 3–4 anther slices bombarded by a particle gun with DNA precipitated onto 1.8 μm tungsten beads. See, for instance, McCormick, et al., 1991. Each shot contained 0.5 μg of DNA. Dark blue-staining spots were observed on anther slices and in individual microspores, indicating that transient expression of the GUS gene had occurred in microspores. The source of spots that were observed occasionally on the anther surface could not be distinguished as to whether they arose from anther cells or stray microspores. However, in additional tests with isolated microspores and leaves, transient expression was confirmed for uidA and luciferase gene fusions in microspores. Transient assays of the luciferase constructs in leaf pieces demonstrated that no gene expression activity of the microspore-specific control sequences was observed in leaves, using the most sensitive assay available (luciferase-catalyzed luminescence detection).

Example 5: Preparation of genetic constructs for microspore-specific expression of genes for insect control or male sterility This example illustrates genetic engineering methods for producing constructs that provide microspore-specific gene expression of heterologous genes, such as genes that effect insect control or male sterility, in transgenic plants.

To provide constructs for microspore-specific expression of genes encoding desired proteins, for instance, a selected insect-control gene or male sterility gene, a DNA segment comprising microspore-specific regulatory sequences of this invention is operatively linked to a heterologous gene, and to 3'-non-translated sequences, as needed, for providing translational and transcriptional control appropriate for the selected heterologous gene. The regulatory sequences are fused with heterologous gene sequences, for example, by modifying the beginning of the open reading frame of the heterologous gene to include a restriction enzyme cleavage site. Advantageously, this cleavage site is an NcoI site or another site compatible for ligation with an NcoI site, because the sequences of such sites comprise an ATG translation start codon.

A variety of genotypes were used for this example wherein xanthi tobacco transformations were performed at the 10 day germination stage.

The constructs are described as follows:
pPHI3621+pPHI1285 [QM, maize sense+BAR]
pPHI3622+pPHI1285 [QM, maize antisense+BAR]
pPHI4722+pPHI1285 [QM, human sense+BAR]
pPHI4723+pPHI1285 [QM, human antisense+BAR]
pPHI4280+pPHI1285 [QMUS+BAR]
pPHI265+pPHI1285 [GUS+BAR]
pPHI1285 [BAR]

To achieve transformation, a particle gun bombardment was used, a GE Helium gun and 650PSI rupture disks.

One bombardment was done per sample, for a total of 0.1 μg.

Tobacco was germinated and observed in vitro on 272 medium for 10–14 days before the following steps. One day before the experiment, cotyledons and first leaves were cut into halves and placed on sterile filters containing 1.5 ml of 530 medium+0.25 M sorbitol. Incubation was done at 28° C. in the dark overnight. Leaf material was dissected under liquid medium to prevent desiccation. Eight leaf sections per plate were cultured, 5 plates were prepared per QM transformation, and 3 plates were prepared per control transformation.

Following bombardment, all samples were maintained on the original filters for 2 days before transferring them to selection medium.

After 48 hours, tissue was transferred to 526+Basta (526H) medium, leaving leaf tissue on the filters. Colony recovery generally occurred at 2–3 weeks post bombardment.

After 4 weeks, cotyledons/colonies were transferred to 528S medium. Plantlets from transformed colonies were cut off of the base callus and transferred to 272N medium to allow for root formation to occur. When roots were well established, plants were transferred to greenhouse for maturing.

The results were as follows:

126 colonies were recovered from all DNA treatments this study. PCR analysis was completed on 50 total colonies by randomly sampling 12 from each of the DNA treatments. Data from this analysis are shown below:

| DNA Treatment | Percent PCR + | Percent Plant Recovery |
|---|---|---|
| pPHI3621/pPHI1285 | 90% | 14.3% |
| pPHI3622/pPHI1285 | 62.5% | 20% |
| pPHI4722/pPHI1285 | 66.7% | 16.6% |
| pPHI4723/pPHI1285 | 75% | 28.6% |
| pPHI4280/pPHI1285 | *n/a | n/a |
| pPHI265/pPHI1285 | 100% | 100% | pPHI4280/pPHI1285 was sampled for PCR and analyzed, however, due to an endogenous tobacco sequence that was amplified with the primers, no further analysis or plant maturation was completed.

Differences in growth rates were observed at 6 weeks post bombardment. The observation most notable was that colonies recovered from transformations with pPHI3621/pPHI1285 and pPHI3622/1285 showed established colony death, especially from the pPHI3622/pPHI1285 treatment. No noticeable differences in growth were noted for the other transformations when compared to the control, pPHI265/pPHI1285 colonies.

Example 6: Stable BMS transformation to evaluate the effect and expression of QM gene in sense and antisense orientation and in the GRP/GRE inducible gene system.

The genotype used was BMS P-38 maize suspensions.
DNA constructs were
pPHI4719+pPHI1285 [35S-QM sense+35S-BAR]
pPHI4720+pPHI1285 [35S-QM sense+35S-BAR]
pPHI4718+pPHI4740+pPHI1285 [NOS-GRP+GRE-QM sense+35S-BAR]
DP1285 [35S-BAR]
Particle gun bombardment was used (a GE helium gun, and 650PSI ruptured disks).

One bombardment was done per sample.

One day after subculture, liquid was vacuumed off the cells and 2 grams of material was resuspended in 20 ml 237+0.25 M sorbitol medium.

Cells were incubated at 28° C. on shaker apparatus for 2–4 hours.

0.5 ml of cells were placed onto double layers of Whatman filters moistened with 1.5 ml 237+0.25 M sorbitol medium. The cell density per plate was about 50 mg.

6 samples were completed for each DNA treatment, including 2 samples as unshot controls.

Following bombardment, filters with cells were transferred to 115 medium and returned to the dark at 28° C. for 48 hours.

Cells were transferred to 306E selection medium after 48 hours by scraping the cells off the filter, resuspending them in 2 ml of 237 medium, and plating them in 1 ml per plate for each sample.

Colony recovery was monitored. When a colony was identified, it was separated from the others to maintain identity.

Induction assays may be performed after PCR analyses confirms presence of genes in transgenic colonies.

Colony recovery occurred from all transformations in this example, however, the majority of recovery came from the DP1285 positive control treatment. Data for colony recovery is shown below:

| DNA Treatment | *N | Colonies Recovered |
|---|---|---|
| pPHI4719/DP1285 | 9 | 3 |
| pPHI4720/DP1285 | 11 | 4 |
| pPHI4718/DP4740/DP1285 | 11 | 22 |
| pPHI1285 | 11 | 44 |

*N denotes the number of samples bombarded per DNA treatment.

Both the 35S sense and antisense constructs for the QM gene were toxic to BMS colony recovery.

Example 7: Using a Maize Tapetum Specific Promoter for Transformation

Experiment Protocols

Repetition 1, 2, . . . and 5:

Goal: Recover transgenic colonies, plants and progeny of maize resistant to Basta/Bialaphos and expressing GUS driven by the tapetum specific SGB6g1 promoter.

Genotype: 54-68-5 B1-1 (Repetition 1) or 54-68-5 161F3 (Repetition 2)54- 68- 5 161F4 (Repetition 5)

Medium: 237 liquid suspension medium for maize 115, callus maintenance medium for maize 115E, callus 5 mg/L Basta selection medium 115B, callus 3 mg/L Bialaphos selection medium Tissue Treatment Sieve cells through 710 um mesh one day after subculture Resuspend in 237+3% PEG at 50 mg/ml plate density Incubate in 3% PEG overnight Plate cells, 0.5 ml/plate onto glass filters 934-AH atop a Whatman filter moistened with 1 ml 237+3% PEG medium Transfer cells on glass filter to 115 medium following bombardment Particle gun bombardment DuPont helium gun (Repetitions 1 and 5)

650 PSI rupture disks (Repetitions 1 and 5)

DuPont PDS-1000 gun (Repetition 2)

0.230" stopping plates, Acetyl macro-projectiles (Repetition 2)

One bombardment per sample (Repetitions 1 and 5)

Two bombardments per sample (Repetition 2)

Pioneer tungsten modified DNA protocols, specific to each gun

DNA:

pPHI687+DP610 pPHI460+DP610 pPHI1952+DP610 pPHI2125+DP610

Treatment/Assay following bombardment

Look for R gene expression 24–48 hours post bombardment

Transfer samples to 115E (repetitions 1) 48 hours post bombardment. Transfer samples to 115B (repetition 2 and 5) 7 days post bombardment Transfer cells off filters 2 weeks following transfer to selection PCR assay colonies for reporter gene prior to plant regeneration Maintain samples at 28° C. in the dark Repetition 1

PCR assays were completed on 16 independent colonies recovered on 5 mg/L Basta selection. One colony, #9 plate 1CZ, DP610+DP2125 was PCR positive for GUS (DP2125). All colonies were Type I phenotypes-however, the nonselected positive control also became a Type I phenotype. This phenotype tends to be common in the 54-68-5 B1-1 line. After 12 weeks on 5 mg/L Basta selection, all PCR negative colonies were discarded along with all remaining nonembryogenic tissue. Colony 2 from Sample #9 plate 1 was transferred to 288E (Regeneration medium+5 mg/L Basta). Eight colonies remained to be PCR assayed for the presence of the GUS gene. Of these eight colonies, three were PCR positive for GUS from either the translational fusion (DP2125) or the transcriptional fusion (DP1952).

Repetition 5

PCR assays were completed on nine independent colonies recovered on 3 mg/L Bialaphos selection. All colonies were PCR positive for the GUS gene, indicating the presence of either DP2125 or DP1952. Gene controls used in this experiment (DP460) have yielded 9 stable transformants, all of which have areas that stain blue in a GUS cytochemical assay. Growth was much faster in the gene controls than in the transgenics recovered from the SGB6gl:GUS constructs.

After 12 weeks under selection pressure, only fast growing, embryogenic colonies were kept—all other material being discarded. Colonies testing PCR positive were transferred to regeneration medium for plant recovery. Basta enzyme assays were completed on a portion of the colonies. Results shown in the data table do not indicate a high degree of transgenics actively showing resistance to Basta. From previous work and other researchers' experiences with this assay, a more reliable measure of transformation has become looking for the cell morphology of the recovered colonies to closely resemble that of the nonselected controls plus the rate of growth the recovered colonies exhibit.

Tungsten/DNA Protocl for DuPont Helium Gun

Weigh 60 mg 1.8 µm tungsten: put into 15 ml centrifuge tube Add 2 ml 0.1 M HnO$_3$: Sonicate on ice for 20 minutes Withdraw HNO$_3$: Add 1 ml sterile deionized water and transfer sample to a 2 ml Sarstedt tube. Sonicate briefly Centrifuge to pellet particles Withdraw H$_2$O: Add 1 ml 100% EtOH—Sonicate briefly Centrifuge to pellet particles Withdraw H$_2$O: Add 1 ml 100% EtOH—Sonicate briefly Centrifuge to pellet particles Withdraw EtOH. Add 1 ml sterile deionized water. Sonicate. Pipet 250 µl of suspension into 4, 2 ml tubes. Add 750 µl of sterile deionized H$_2$O to each tube.

Freeze tungsten sample between use.

To prepare DNA

Pipet 50 µl tungsten/H$_2$O suspension into 1.5 ml tube (Sonicate first) Add 10 µg DNA, Mix Add 50 µg 2.5 M CaCl$_2$. Mix Add 20 µl 0.1 M Spermidine. Mix Sonicate briefly. Centrifuge for 10 seconds at 10,000 RPM. Withdraw supernatent. Add 250 µl 100% EtOH. Sonicate briefly. Centrifuge at 10,000 RPM for 10 seconds Withdraw supernatent. Add 60 µl 100% EtOH.

Example 8: Construction of Plasmids Containing The Maize QM Gene

Figure 4:
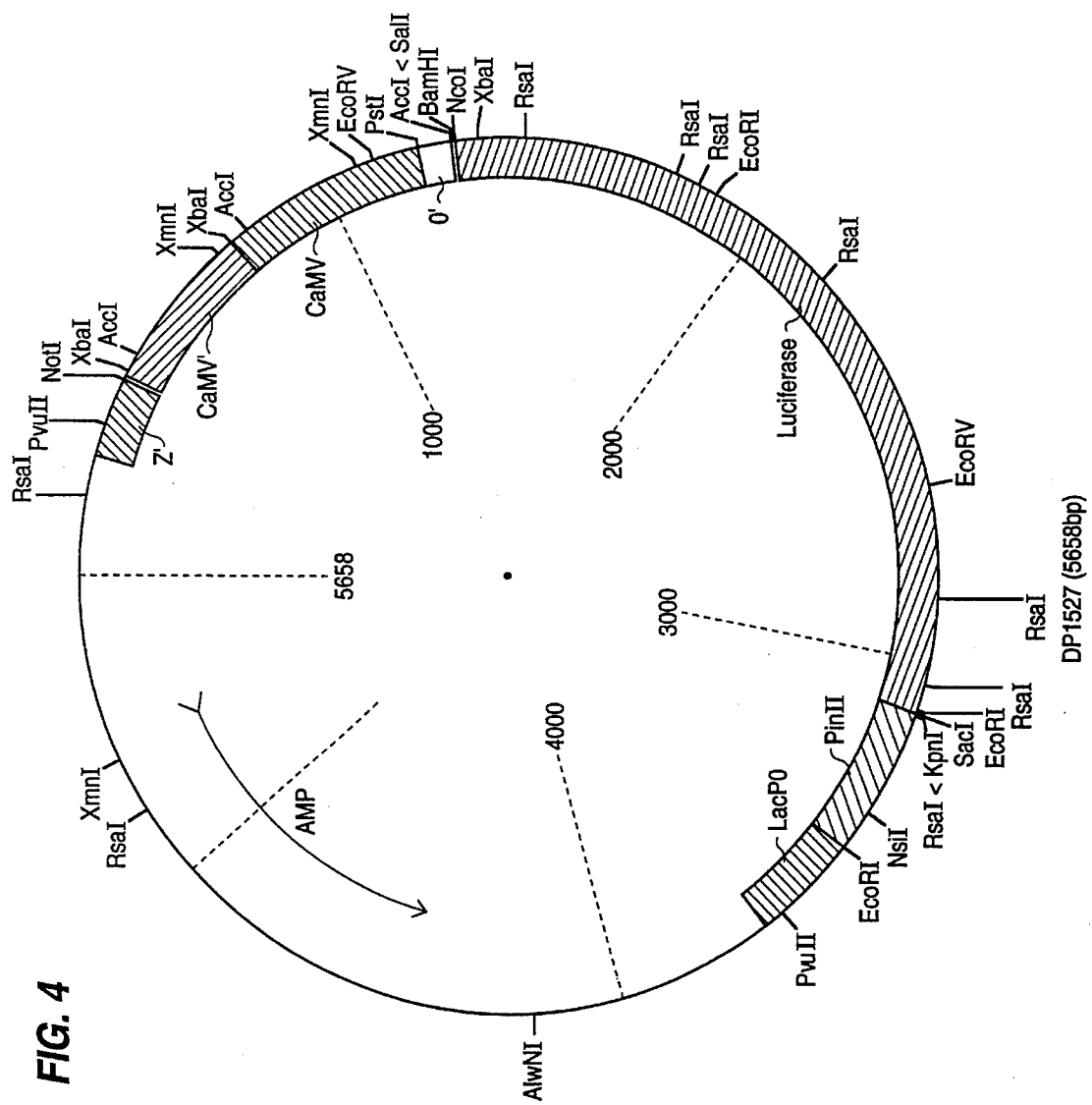
FIG. 4. Restriction map of Dp1527.

Plasmid pPHI3621 (FIG. 3) which expresses the QM gene in the sense orientation was constructed using pPHI1527 as one parent. pPHI1527 (FIG. 4) contains the plasmid pUC18 as the backbone (Yanisch-Perron, C., Vieira, J. and Messing J., 1985, "Improved M13 cloning vectors and host strains: Nucleotide sequences of the M13mp18 and pUC19 vectors."

Figure 5:
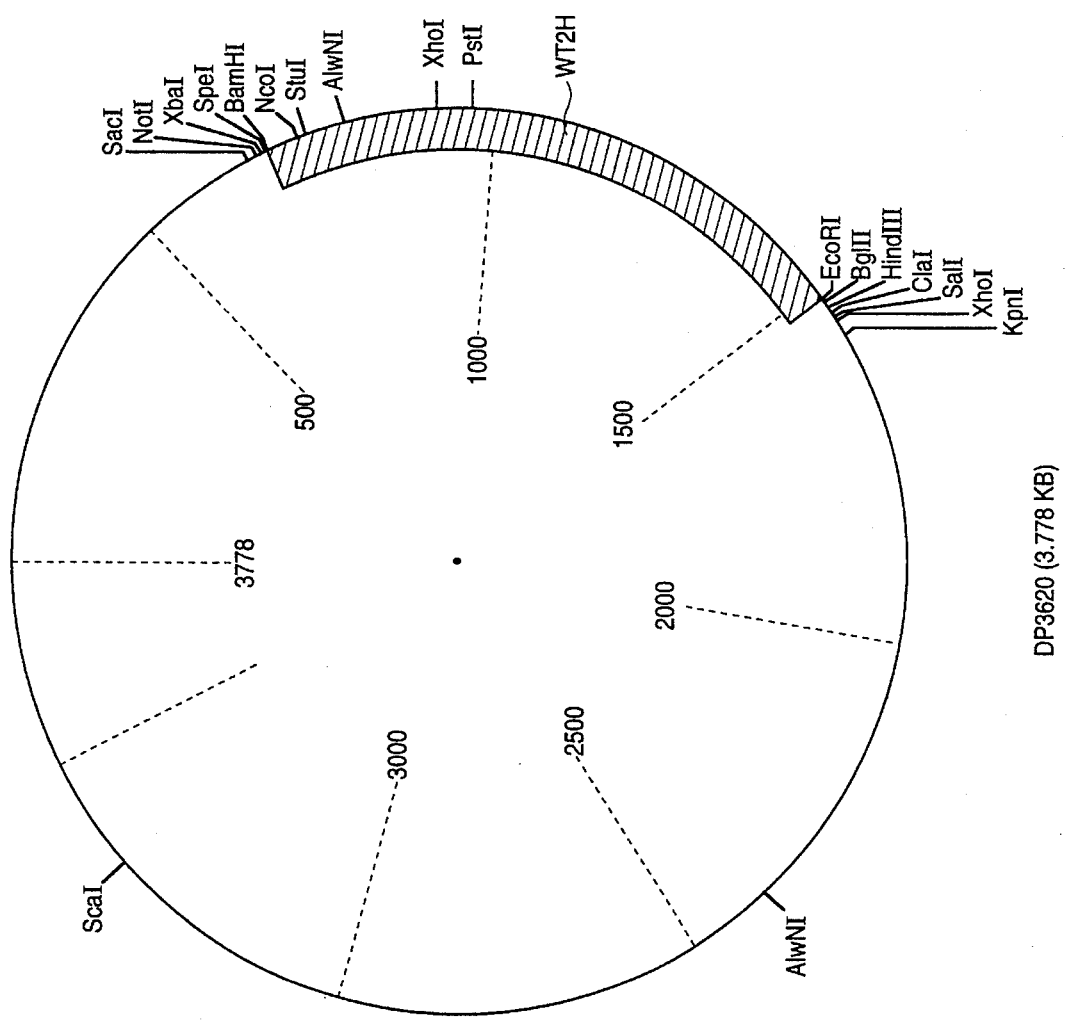
FIG. 5. Restriction map of Dp3620.
Figure 6:
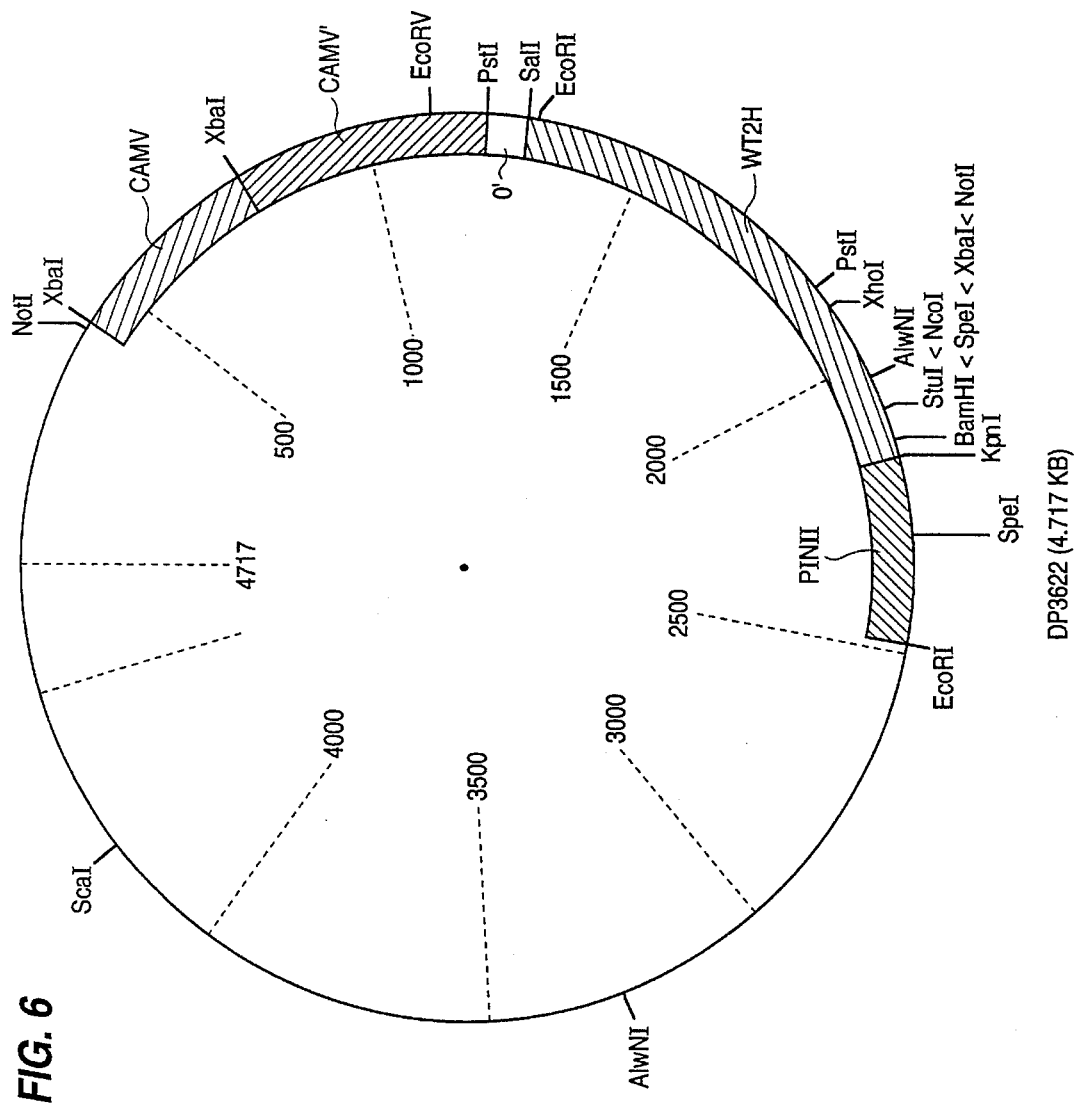
FIG. 6. Restriction map of Dp3622.

Gene 33:103–119) which contains the restriction sites necessary for cloning and the ampicillin resistance gene as a selectable marker. It also contains the cauliflower mosaic virus (CaMV) 35S promoter and enhancer sequences (Gardner, R. C., Howarth, A. J., Hahn, P., Brown-Luedi, M., Shepherd, R. J. and Messing, J. C., 1981, "The complete nucleotide sequence of an infectious clone of cauliflower mosaic virus by M13mp7 shotgun sequencing." *Nucleic Acids Res.* 9:2871–2888), the tobacco mosaic virus leader sequences, O' (Gallie D. R., Slex, D. E., Watts, J. W., Turner, P. C. and Wilson, T. M. A., 1987, "The 5' leader sequence of tobacco mosaic virus RNA enhances the expression of foreign gene transcripts in vitro and in vivo." *Nucleic Acids Res.* 8:3257–3273), the firefly luciferase reporter gene (OW, D., Wood, K. V., DeLuca, M., de Wet, J. R., Helinski, D. R., and Howell, S. H., 1986, "Transient and stable expression of the firefly luciferae gene in plant cells and transgenic plants." *Science* 234:856–859) and the PinII transcription terminator sequences (Hynheung, A., Mitra, A., Choi, H. K., Costa, M. A., An, K., Thornburg, R. W. and Ryan, C. A., 1989, "Functional analysis of the 3' control region of the potato wound-inducible proteinase inhibitor II gene." *Plant Cell* 1:115–122). The second parent of pPHI3621 was pPHI3520, which pBluescript KS- containing the maize QM gene (FIG. 5). pPHI3621 was generated by digestion of both pPHI3620 and pPHI1527 with NcoI and KpnI and isolation of the insert band from pPHI3620 and the larger plasmid band from pPHI1527 on low melting point (LMP) agarose gels. This strategy replaced the luciferase gene with the maize QM gene. The bands were pooled and ligated to form pPHI3621.

pPHI3622 (FIG. 6), which expresses the antisense of the maize QM gene was constructed using pPHI1527 and pPHI3620 as parents, but by digestion of both with SalI and SacI. The insert band from pPHI3620 and the larger plasmid band from pPHI1527 was isolated from LMP agarose gels, the fragments were pooled and ligated. Again, this replaced the luciferase gene with maize QM gene in the antisense orientation.

Figure 7:
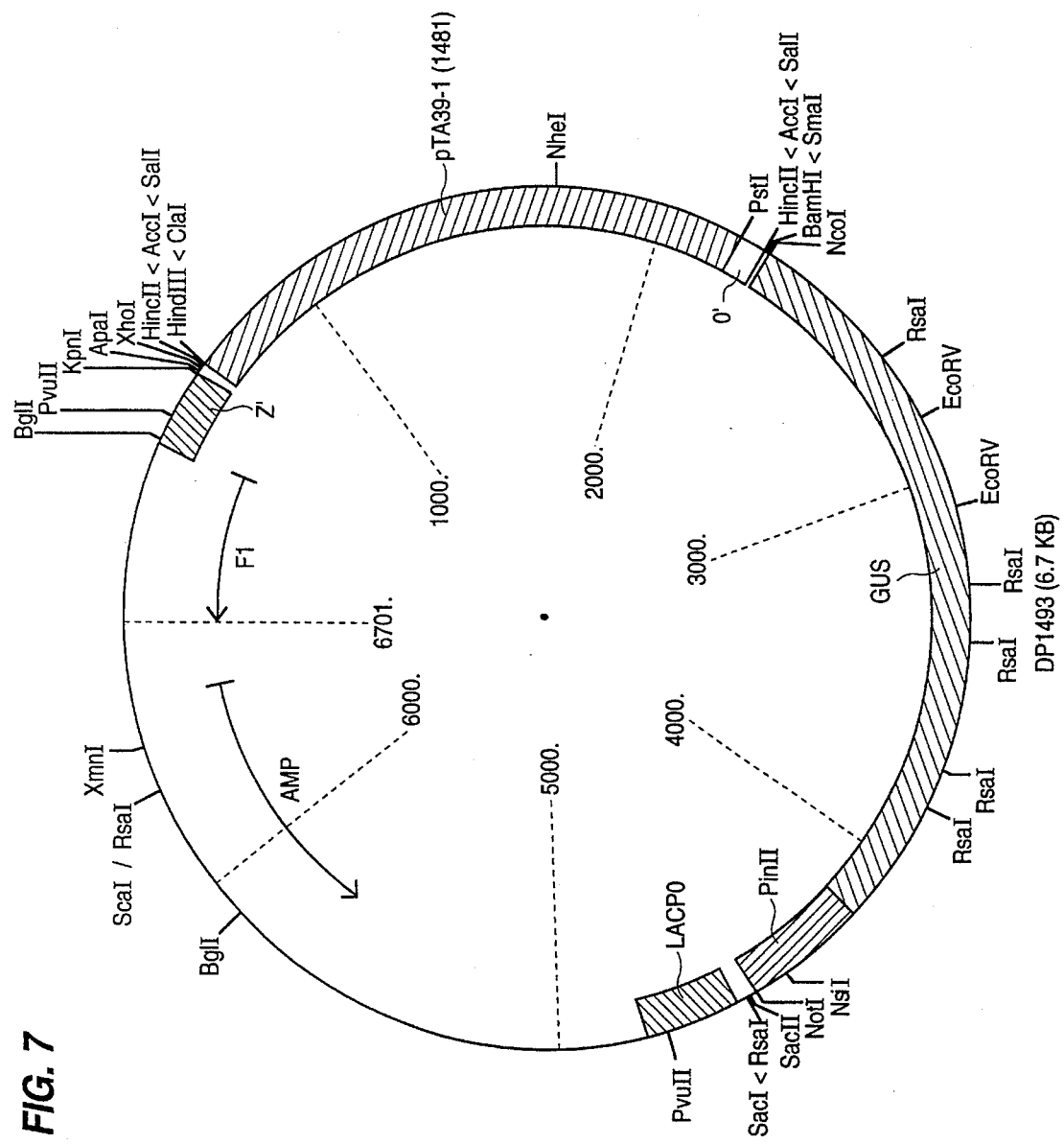
FIG. 7. Restriction map of Dp1493.
Figure 8:
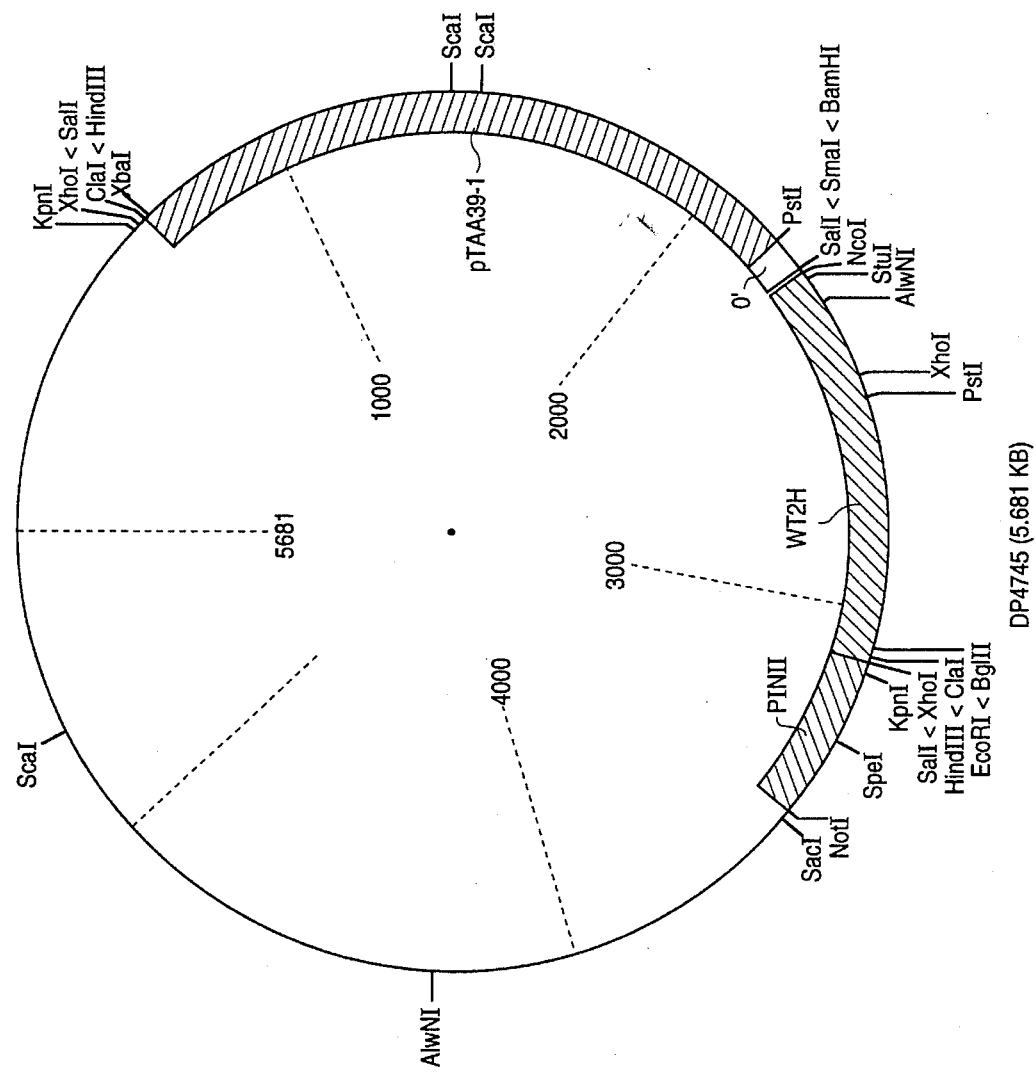
FIG. 8. Restriction map of Dp4745.
Figure 9:
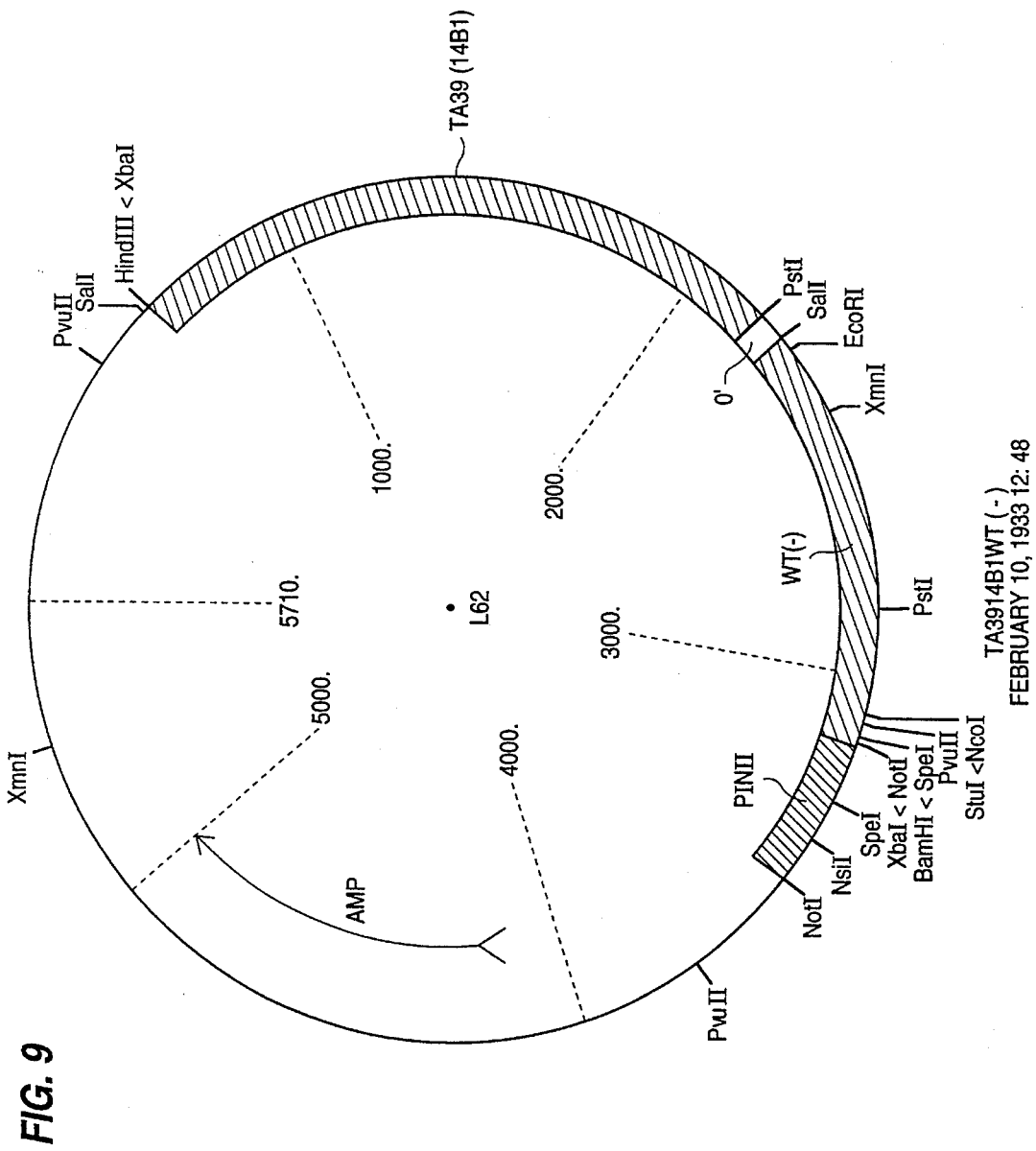
FIG. 9. Restriction map of TA3914BIWT(–).

Tissue specific expression vectors were constructed in the same manner except that the CaMV constitutive promoter was replaced with the TA39 anther specific promoters, 14B1 and 8B3 (Garnaat, CW. and Huffman, G., 1991, "Isolation and transient assay of tobacco anther specific promoters." Abstracts: The International Society for Plant Molecular Biology. Tucson, Ariz., Oct. 1991). pPHI1493 (FIG. 7) containing the 14B1 promoter was digested with NcoI and NsiI as was pPHI3621 (parent 2). The small insert band from pPHI3621 and the larger plasmid band were isolated by LMP agarose gel electrophoresis, were pooled and ligated. This yielded pPHI4745 (FIG. 8) which contained the maize QM gene in the antisense orientation with the 14B1 promoter. The maize QM antisense construct was made by digestion of pPHI4745 with SmaI and NsiI and digestion of pPHI3622 with SalI (which was filled in with Klenow fragment) and NsiI. The large plasmid band from pPHI4745 and the insert band from pPHI3622 were isolated by LMP gel, pooled and ligated. This yielded the plasmid L62 (FIG. 9).

Figure 10:
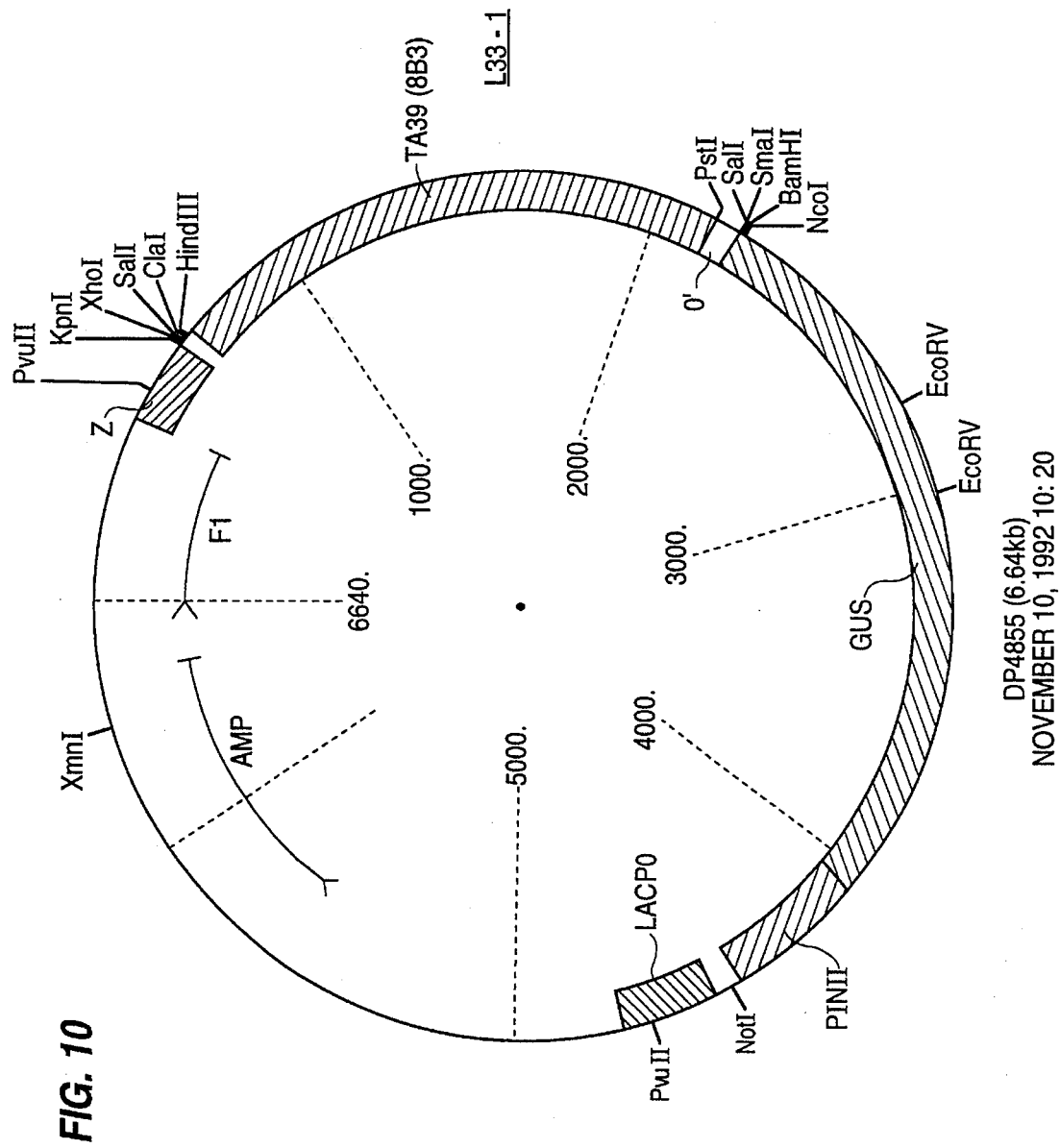
FIG. 10. Restriction map of Dp4855.
Figure 11:
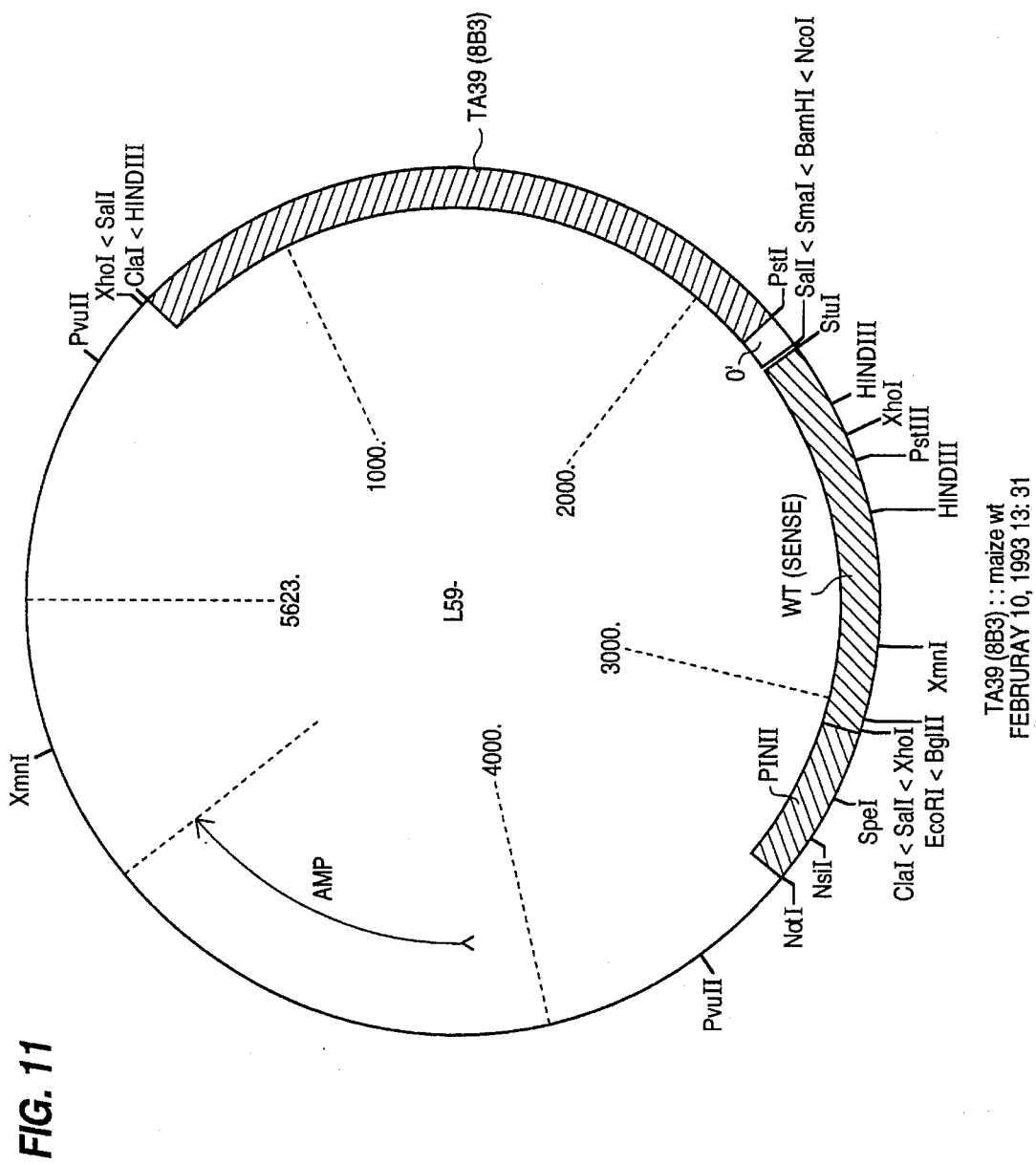
FIG. 11. Restriction map of TA39(BB3)::maize wt.
Figure 12:
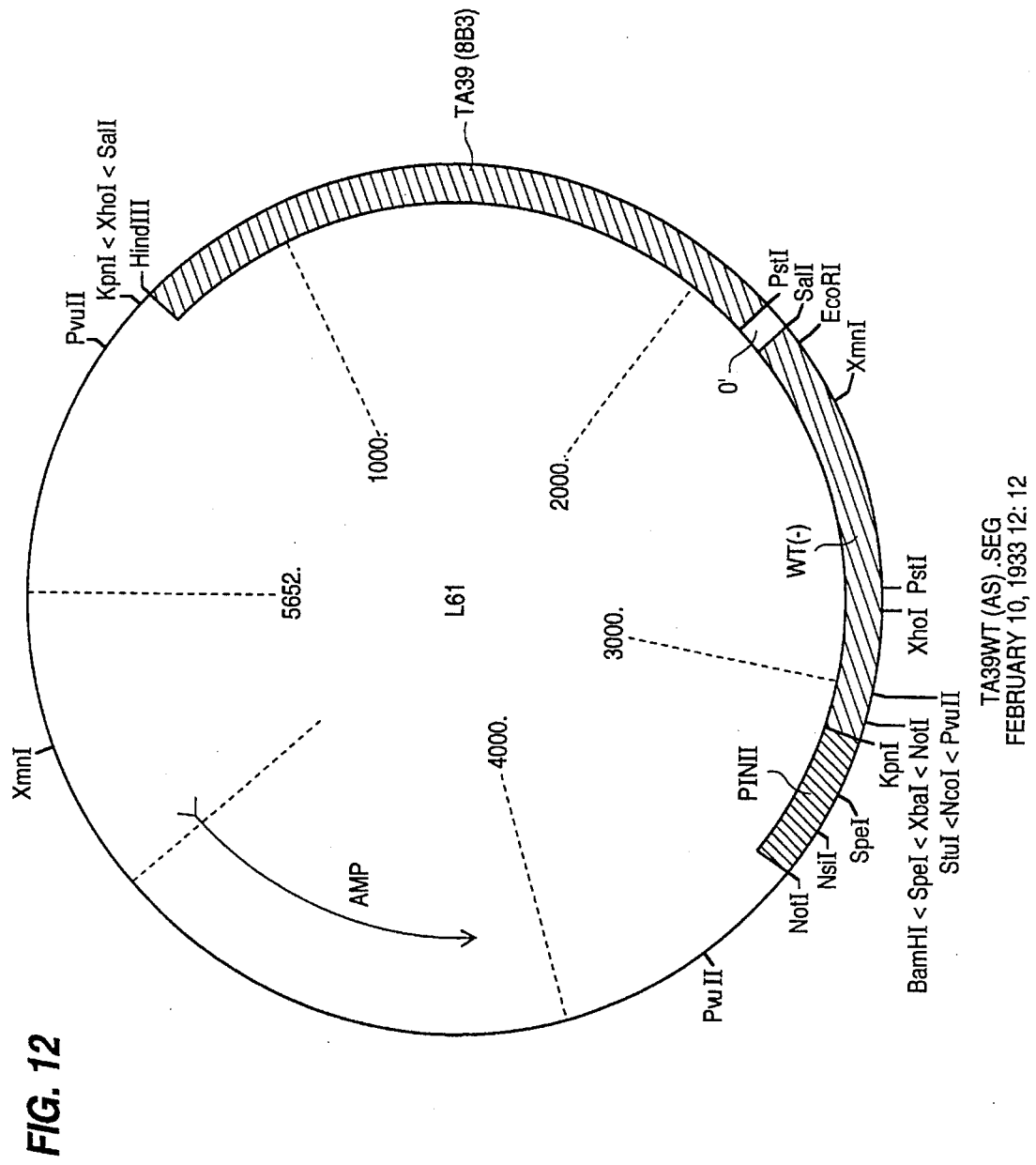
FIG. 12. Restriction map of TA39WT(AS).SEQ.

The expression vectors containing the 8B3 anther specific promoter were constructed by digestion of pPHI4855 (FIG. 10) with BamHI and NotI. pPHI4855 contained all of the above described sequences with the additional sequences encoding the B-glucuronidase gene (Walden, R and Schell, J., 1990, "Techniques in plant molecular biology-progress and problems." *Eur. J. Biochem.* 192:563–576). The other parent, pPHI4745 was also digested with BamHI and NotI. The large plasmid band from the pPHI4855 and the insert band from pPHI4745 were purified from LMP agarose, pooled and ligated. The resulting plasmid, L59 (FIG. 11) contained the maize QM in the sense orientation driven by the anther specific promoter 8B3. The antisense construct was made by digestion of pPHI4855 with SmaI and NsiI and pPHI3622 with SalI (then filled in with Klenow fragment) and NsiI. The large plasmid band from pPHI4855 and the insert band from pPHI3622 were isolated from LMP agarose gel, pooled and ligated. This gave L61 (FIG. 12) the antisense orientation of the maize QM gene behind the 8B3 promoter.

Materials and Methods

USE OF QM GENE IN SENSE ORIENTATION: The nucleotides segment of the QM gens isolated from maize or other plant sources is fused at its upstream (5') end to a promoter which allows expression of the sense strand in a particular target plant cell and is fused at its downstream (3') end to suitable transcription terminator and polyadenylation signals known to function in that cell. Preferred promoters include those that are known to direct expression in the desired target cell, which includes "constitutive" promoters such as 35S from caMV and the promoter from the ubiquitin gens that are known to direct expression in a wide variety of plant cell types. 35S is likely to direct expression in both monocots such as corn and dicots such as tobacco and canola. However, the ubiquitin promoter for tobacco preferably is derived from a dicot source. The ubiquitin promoter for use in monocots such as corn preferably is derived from a monocot source. Other suitable promoters include those which are known to be inducible under specific conditions, such as in response to particular chemical treatments for example, an herbicide.

Terminator/polyadenylation signals include those that are known to function in the target cell of interest. Preferred are signals from genes such as pinII (proteinase inhibitor II from potato) or T-DNA genes such as OCS or NOS, which are known to function in a wide variety of plant cell types, including those of dicots and monocots such as corn. When the target cell is from a monocot like corn, it is preferred, but not necessarily required, that an intron from a monocot gene be inserted between the promoter and the QM gene. Examples would be an intron (such as intron 1 or 6) from the Adh1 gene of corn.

USE OF MAIZE QM GENE IN ANTISENSE ORIENTATION: The antisense form of the QM gene is fused at its upstream (5') end to a promoter which directs expression in a particular target plant cell, and is fused at its downstream (3') end to suitable transcription terminator and polyadenylation signals also known to function in that cell. An embodiment of a target cell in this case is a cell in which the QM gene or a gene highly homologous to the QM gene is known to be expressed so that the antisense works effectively. Preferred promoters encompass those that are known to direct expression in the desired target cell, suitable candidates include "constitutive" promoters such as 35S and the promoter from the ubiquitin gene that are known to direct expression in a wide variety of plant cell types. 35S is expected to express in both monocots such as corn and dicots such as tobacco and canola. However, the ubiquitin promoter for tobacco is preferably from a dicot source, and the ubiquitin promoter for use in monocots such as corn is preferably from a monocot source. Other preferred promoters include those which are known to be inducible under specific conditions, such as in response to a particular chemical treatment for example, a herbicide. It is preferred that the antisense construct include the entire QM gene or at least several hundred nucleotides from the 5' end of the gene.

USE OF QM GENE IN ANTISENSE ORIENTATION: The nucleotide segment of the antisense form of the QM gene is fused at its upstream (5') end to a promoter which is known to be specific for, or show a strong preference for expression in, a tissue or cell critical for pollen development. An example of a suitable tissue is the anther. An example of a suitable cell is a tapetal cell or a developing microspore. The segment is fused at its downstream (3') end to suitable transcription terminator and polyadenylation signals also known to function in the cell or tissue. The target cell is a cell in which the QM gene or a gene highly homologous to the QM gene is known to direct expression so that the antisense works effectively.

TRANSFORMATION METHODS: Transformation methods for dicots include a number of different well-known methods for direct DNA delivery. Preferred is particle biolistics bombardment of leaf explants. Other methods include Agrobacterium delivery to explants; Agrobacterium cocultivation of protoplasts; electroporation, PEG uptake or other direct DNA delivery into protoplasts, and the like. A preferred method for monocots such as corn is delivery of DNA to the treated cells by bombardment, but other methods such as electroporation can also be used.

Cells of a plant are transformed with the foreign DNA sequence of this invention in a conventional manner. If the plant to be transformed is susceptible to Agrobacterium infections, it is preferred to use a vector containing the foreign DNA sequence, which is a disarmed Ti-plasmid. The transformation can be carried out using procedures described, for example, in EP 0,116,718 and EP 0,270,822. Preferred Ti-plasmid vectors contain the foreign DNA sequence between the border sequences, or at least located upstream of the right border sequence. Of course, other types of vectors can be used for transforming the plant cell, using procedures such as direct gene transfer (as described for example in EP 0,2370,356, PCT publication WO/85/01856 and EP 0,275,069), in vitro protoplast transformation (as described for example in U.S. Pat. No. 4,684,611), plant virus-mediated transformation (as described for example in EP 0,067,553 and U.S. Pat. No. 4,407,956) and liposome-mediated transformation (as described for example in U.S. Pat. No. 4,536,475).

If the plant to be transformed is corn, recently developed transformation methods are suitable such as the methods described for certain lines of corn by Fromm et al. (1990) Bio/Technology 8: and 833 and Gordon-Kamm et al. (1990) The Plant Cell 2: 603.

If the plant to be transformed is rice, recently developed transformation methods can be used such as the methods described for certain lines of rice by Shimamoto et al. (1990) Nature 338: 274, Datta et al. (1990) Bio/Technology 8, 736, Christou et al. (1991) Bio/Technology 9, 957 and Lee et al. (1991) PNAS 88: 6389.

If the plant to be transformed is wheat, a method analogous to those described above for corn or rice can be used. Preferably for the transformation of a monocotyledonous plant, particularly a cereal such as rice, corn or wheat, a method of direct DNA transfer, such as a method of biolistic transformation or electroporation, is used. When using such a direct transfer method, it is preferred to minimize the DNA that is transferred so that essentially only the DNA sequence of this invention, the QM maize gene, is integrated into the plant genome. In this regard, when a DNA sequence of this invention is constructed and multiplied in a plasmid in a bacterial host organism, it is preferred that, prior to transformation of a plant with the DNA sequence, plasmid sequences that are required for propagation in the bacterial host organism, such as on origin of replication, an antibiotic resistance gene for selection of the host organism, and the like, be separated from the parts of the plasmid that contain the foreign DNA sequence.

PROTOCOL FOR CORN TRANSFORMATION TO RECOVER STABLE TRANSGENIC PLANTS

Day—1 Cells places in liquid media and slaved (710 um). 100–200 mg of cells collected on 5.5 cm glass fiber filter over an area of 3.5 cm. Cells transferred to media and incubated media overnight.

Day—8 Filter and cells removed from media, dried and bombarded. Filter and cells placed back on media.

Day—5 Cells on filter transferred to selection media (3 mg bialophos).

Day—12 Cells on filter transferred to fresh selection media.

Day—19 Cells scraped from filter and dispersed in 5 ml of selection media containing 8.6% low melting point sea agarose. Cells and media spread over the surface of two 100 mm×15 mm plates containing 20 ml of gel-rite solidified media.

Day—40 Putative transformants picked from plate.

Day—61 Plates checked for new colonies.

RNA ANALYSIS: Total cellular RNA was prepared from B73 seedlings seven days following planting by the protocol of Chomczynski and Sacchi (1987). Poly (A)+RNA was purified from leaf homogenates using the PolyAtract 1000 system (Promega). Northern blots were done as previously described (Thomas, 1980).

References

1. Call et al., 1990, "Isolation and characterization of a zinc finger polypeptide gene at the human chromosome 11 Wilms' tumor locus". *Cell*, 60:509–520.
2. Chomczynski et al., 1987, "Single-step method of RNA isolation by acid guanidinium thiocyanate-phenolchloroform extraction." *Anal. Biochem.*, 162:156–159.
3. Colasanti, J. et al., (1991), "Isolation and characterization of cDNA clones encoding a functional p34cdc2 homologue from Zea mays", *Proc. Natl. Acad. Sci. USA* 88:3377–3381
4. Devereux et al., 1984, "A comprehensive set of sequence analysis programs for the VAX." *Nucleic Acids Res.* 12:387–395.
5. Edwards et al., (1990), "Cell-specific gene expression in plants." *Ann. Rev. Genet* 24:275–303.
6. Gessler et al., 1990, "Homozygous deletion in Wilms' tumors of a zinc-finger gene identified by chromosome jumping." *Nature*, 343:774–778.
7. Klein et al., (1989), "Regulation of anthocyanin biosynthetic genes introduced into intact maize tissues by microprojectiles." *Proc. Natl. Acad. Sci. USA* 86:6681–6685.
8. Kuhlmeier et al., (1987), "Regulation of gene expression in higher plants." *Ann Rev. Plant Physiol.* 38:221–257.
9. Schmidt et al., (1992), "Opaque2 is a transcriptional activator that recognizes a specific target site in 22-kd zein genes." *Plant Cell* 4:689–700.
10. Thomas et al., 1980, "Hybridization of denatured RNA and small DNA fragments transferred to nitrocellulose." *Proc. Natl. Acad. Sci. USA.*, 77:5201–5205.
11. Ueda et al., (1992), "Mutations of the 22- and 27-kd zein promoters affect transactivation by the Opaque2 protein." *Plant Cell* 4:701–709.
12. van den Ouweland et al., 1992, "Identification and characterization of a new gene in the human Xq28 region". *Human Mol. Genet.*, 1:269–273.

What is claimed is:

1. A chimeric plant QM gene comprising a DNA sequence encoding a plant QM protein, wherein said DNA sequence is operably joined to flanking regulatory regions not naturally associated with the plant QM protein coding sequence.

2. The chimeric plant QM gene of claim 1, wherein said DNA sequence comprises the nucleotide sequences at positions 30–100, 210–250, and 330–400 according to the nucleotide sequence numbering of SEQ ID NO: 1.

3. The chimeric plant QM gene of claim 2, wherein said DNA sequence comprises the nucleotide sequence according to SEQ ID NO: 1.

4. An isolated vector comprising the coding sequence of the chimeric plant QM gene of claim 1.

5. The vector of claim 4, wherein said regulatory region comprises a tissue-specific promoter.

6. The vector of claim 4, wherein said regulatory region comprises a cell-specific promoter.

7. A method of making plant QM protein, comprising the steps of transforming a plant cell with the vector of claim 4; regenerating a plant from said transformed plant cell; and expressing said chimeric plant QM gene so as to produce the encoded QM protein in said plant.

8. A plant cell comprising the chimeric plant QM gene of claim 1.

9. A tissue or cell culture comprising the plant cell of claim 8.

10. A plant seed comprising the chimeric plant QM gene of claim 1.

11. A plant comprising a chimeric plant QM gene which is produced by the method of claim 7.

* * * * *

UNITED STATES PATENT AND TRADEMARK OFFICE
CERTIFICATE OF CORRECTION

PATENT NO.   : 5,583,210
DATED        : December 10, 1996
INVENTOR(S)  : John Neill, Dorothy A. Pierce, Andrew M. Cigan It is certified that error appears in the above-indentified patent and that said Letters Patent is hereby corrected as shown below:

Column 4, line 39, please delete "50" and replace it with --51--.

Column 6, line 56, please delete "50 and 61" and replace it with --51 and 60--.

Signed and Sealed this

Twenty-first Day of October 1997

Attest:

BRUCE LEHMAN

Attesting Officer      Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 936 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 42..704

( x i ) SEQUENCE DESCRIPTION: SEQ ID NO:1:

```
GGATCCGCCG ACACCGACTG CCTACCTCAG CTGCCGTCGC C ATG GGC AGA AGG      53
                                              Met Gly Arg Arg
                                              1

CCT GCT AGA TGC TAT CGC CAG ATC AAG AAC AAG CCG TGC CCT AAG TCC    101
Pro Ala Arg Cys Tyr Arg Gln Ile Lys Asn Lys Pro Cys Pro Lys Ser
 5               10                  15                       20

AGG TAC TGC CGT GGT GTC CCT GAC CCC AAG ATC AGG ATC TAC GAT GTC    149
Arg Tyr Cys Arg Gly Val Pro Asp Pro Lys Ile Arg Ile Tyr Asp Val
              25                  30                  35

GGG ATG AAG AGG AAG GGT GTT GAT GAG TTC CCC TAC TGT GTG CAC CTT    197
Gly Met Lys Arg Lys Gly Val Asp Glu Phe Pro Tyr Cys Val His Leu
              40                  45                  50

GTC TCT TGG GAG AGG GAG AAT GTC TCC AGT GAG GCG CTC GAG GCT GCC    245
Val Ser Trp Glu Arg Glu Asn Val Ser Ser Glu Ala Leu Glu Ala Ala
              55                  60                  65

CGC ATT GTC TGT AAC AAG TAC ATG ACC AAG TCT GCA GGA AAG GAT GCC    293
Arg Ile Val Cys Asn Lys Tyr Met Thr Lys Ser Ala Gly Lys Asp Ala
     70                  75                  80

TTC CAC CTT AGG GTC CGG GTT CAC CCG TTC CAT GTC CTC CGT ATC AAC    341
Phe His Leu Arg Val Arg Val His Pro Phe His Val Leu Arg Ile Asn
 85                  90                  95                  100

AAG ATG CTT TCC TGT GCC GGG GCT GAT AGG CTC CAG ACT GGA ATG AGG    389
Lys Met Leu Ser Cys Ala Gly Ala Asp Arg Leu Gln Thr Gly Met Arg
                105                 110                 115

GGT GCC TTT GGC AAG CCT CAG GGC ACC TGT GCT AGG GTG GAC ATT GGT    437
Gly Ala Phe Gly Lys Pro Gln Gly Thr Cys Ala Arg Val Asp Ile Gly
            120                 125                 130

CAG GTC CTC CTT TCC GTG CGC TGC AAG GAC AAC AAT GCT GCC CAT GCC    485
Gln Val Leu Leu Ser Val Arg Cys Lys Asp Asn Asn Ala Ala His Ala
            135                 140                 145

AGC GAA GCT CTG CGT CGC GCT AAG TTC AAG TTC CCT GCC CGC CAG AAG    533
Ser Glu Ala Leu Arg Arg Ala Lys Phe Lys Phe Pro Ala Arg Gln Lys
        150                 155                 160

ATC ATT GAG AGC AGA AAG TGG GGC TTC ACC AAG TTC AGC CGC GCT GAC    581
Ile Ile Glu Ser Arg Lys Trp Gly Phe Thr Lys Phe Ser Arg Ala Asp
165                 170                 175                 180

TAC CTG AAG TAC AAG AGC GAG GGC AGA ATT GTT CCT GAT GGT GTC AAC    629
Tyr Leu Lys Tyr Lys Ser Glu Gly Arg Ile Val Pro Asp Gly Val Asn
                185                 190                 195

GCA AAG CTG CTC GCC AAC CAC GGC AGA CTT GAG AAG CGT GCT CCT GGG    677
Ala Lys Leu Leu Ala Asn His Gly Arg Leu Glu Lys Arg Ala Pro Gly
            200                 205                 210
```

```
AAG GCT TTC CTC GAT GCC GTT GCT TAAGTGCGGA TGCGAATCCT GACGTTTTGC        731
Lys Ala Phe Leu Asp Ala Val Ala
        215                 220

TTTAGCGTAT CTTACTTTGC TTCGTGGAAC ATGAATTTCA AGTGTTTTGA GGGTATTACA        791

GTGCCTTATG TGAACTTGCC TATCTTGTGC TGAACATCGG AATGTATCCT CCGAGTATGT        851

TTAATCGCAT TAATTTTATT GGGAAATTGG TTGCGGAACA ATGTCCAATT TAACTCGAAT        911

TTGATTTCAA CACGGTCTTT TCTTT                                             936
```

( 2 ) INFORMATION FOR SEQ ID NO:2:

( i ) SEQUENCE CHARACTERISTICS:
        ( A ) LENGTH: 220 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Arg Arg Pro Ala Arg Cys Tyr Arg Gln Ile Lys Asn Lys Pro
 1               5                  10                  15

Cys Pro Lys Ser Arg Tyr Cys Arg Gly Val Pro Asp Pro Lys Ile Arg
            20                  25                  30

Ile Tyr Asp Val Gly Met Lys Arg Lys Gly Val Asp Glu Phe Pro Tyr
            35                  40                  45

Cys Val His Leu Val Ser Trp Glu Arg Glu Asn Val Ser Ser Glu Ala
    50                  55                  60

Leu Glu Ala Ala Arg Ile Val Cys Asn Lys Tyr Met Thr Lys Ser Ala
65                  70                  75                  80

Gly Lys Asp Ala Phe His Leu Arg Val Arg Val His Pro Phe His Val
                85                  90                  95

Leu Arg Ile Asn Lys Met Leu Ser Cys Ala Gly Ala Asp Arg Leu Gln
            100                 105                 110

Thr Gly Met Arg Gly Ala Phe Gly Lys Pro Gln Gly Thr Cys Ala Arg
            115                 120                 125

Val Asp Ile Gly Gln Val Leu Leu Ser Val Arg Cys Lys Asp Asn Asn
    130                 135                 140

Ala Ala His Ala Ser Glu Ala Leu Arg Arg Ala Lys Phe Lys Phe Pro
145                 150                 155                 160

Ala Arg Gln Lys Ile Ile Glu Ser Arg Lys Trp Gly Phe Thr Lys Phe
                165                 170                 175

Ser Arg Ala Asp Tyr Leu Lys Tyr Lys Ser Glu Gly Arg Ile Val Pro
            180                 185                 190

Asp Gly Val Asn Ala Lys Leu Leu Ala Asn His Gly Arg Leu Glu Lys
            195                 200                 205

Arg Ala Pro Gly Lys Ala Phe Leu Asp Ala Val Ala
    210                 215                 220
```

( 2 ) INFORMATION FOR SEQ ID NO:3:

( i ) SEQUENCE CHARACTERISTICS:
        ( A ) LENGTH: 214 amino acids
        ( B ) TYPE: amino acid
        ( D ) TOPOLOGY: linear ( x i ) SEQUENCE DESCRIPTION: SEQ ID NO:3:

```
Met Gly Arg Arg Pro Ala Arg Cys Tyr Arg Tyr Cys Lys Asn Lys Pro
 1               5                  10                  15
```

-continued

| | | | | | | | | | | | | | | |
|---|---|---|---|---|---|---|---|---|---|---|---|---|---|---|
| Tyr | Pro | Lys | Ser 20 | Arg | Phe | Cys | Arg | Gly 25 | Val | Pro | Asp | Ala | Lys 30 | Ile | Arg |
| Ile | Phe | Asp 35 | Leu | Gly | Arg | Lys | Lys 40 | Ala | Lys | Val | Asp | Glu 45 | Phe | Pro | Leu |
| Cys | Gly 50 | His | Met | Val | Ser | Asp 55 | Glu | Tyr | Glu | Gln | Leu 60 | Ser | Ser | Glu | Ala |
| Leu 65 | Glu | Ala | Ala | Arg | Ile 70 | Cys | Ala | Asn | Lys | Tyr 75 | Met | Val | Lys | Ser | Cys 80 |
| Gly | Lys | Asp | Gly | Phe 85 | His | Ile | Arg | Val | Arg 90 | Leu | His | Pro | Phe | His 95 | Val |
| Ile | Arg | Ile | Asn 100 | Lys | Met | Leu | Ser | Cys 105 | Ala | Gly | Ala | Asp | Arg 110 | Leu | Gln |
| Thr | Gly | Met 115 | Arg | Gly | Ala | Phe | Gly 120 | Lys | Pro | Gln | Gly | Thr 125 | Val | Ala | Arg |
| Val | His 130 | Ile | Gly | Gln | Val | Ile 135 | Met | Ser | Ile | Arg | Thr 140 | Lys | Leu | Gln | Asn |
| Lys 145 | Glu | His | Val | Ile | Glu 150 | Ala | Leu | Arg | Arg | Ala 155 | Lys | Phe | Lys | Phe | Pro 160 |
| Gly | Arg | Gln | Lys | Ile 165 | His | Ile | Ser | Lys | Lys 170 | Trp | Gly | Phe | Thr | Lys 175 | Phe |
| Asn | Ala | Asp | Glu 180 | Phe | Glu | Asp | Met | Val 185 | Ala | Glu | Lys | Arg | Leu 190 | Ile | Pro |
| Asp | Gly | Cys 195 | Gly | Val | Lys | Tyr | Ile 200 | Pro | Ser | Arg | Gly | Pro 205 | Leu | Asp | Lys |
| Trp | Arg 210 | Ala | Leu | His | Ser | | | | | | | | | | |

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ATGGGCAGAA GGCCTGCTAG ATGC                                     24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CAACGGCATC GAGGAAAGCC TTCC                                     24